United States Patent
Kovalsky

(10) Patent No.: US 9,801,715 B2
(45) Date of Patent: Oct. 31, 2017

(54) HEART VALVE PROSTHESIS

(71) Applicant: Medtronic, Inc., Minneapolis, MN (US)

(72) Inventor: Igor Kovalsky, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/266,924

(22) Filed: Sep. 15, 2016

(65) Prior Publication Data

US 2017/0000605 A1     Jan. 5, 2017

Related U.S. Application Data

(62) Division of application No. 13/572,842, filed on Aug. 13, 2012, now Pat. No. 9,468,525.

(51) Int. Cl.
*A61F 2/82* (2013.01)
*A61F 2/24* (2006.01)

(52) U.S. Cl.
CPC .......... *A61F 2/2418* (2013.01); *A61F 2/2436* (2013.01); *A61F 2220/0008* (2013.01); *A61F 2230/0013* (2013.01); *A61F 2230/0069* (2013.01)

(58) Field of Classification Search
CPC ........................................................ A61F 2/82
See application file for complete search history.

(56) References Cited

U.S. PATENT DOCUMENTS

| | | |
|---|---|---|
| 5,957,949 A | 9/1999 | Leonhardt et al. |
| 7,748,389 B2 | 7/2010 | Salahieh et al. |
| 7,947,075 B2 | 5/2011 | Goetz et al. |
| 2003/0036791 A1 | 2/2003 | Philipp et al. |
| 2003/0199963 A1 | 10/2003 | Tower et al. |
| 2003/0199971 A1 | 10/2003 | Tower et al. |

(Continued)

FOREIGN PATENT DOCUMENTS

| | | |
|---|---|---|
| CA | 2827556 | 7/2012 |
| WO | WO2004019825 | 3/2004 |

(Continued)

OTHER PUBLICATIONS

Boudjemline et al., "Steps Toward Percutaneous Aortic Valve Replacement" Circulation 2002; 105; 775-558.

(Continued)

*Primary Examiner* — Matthew Schall

(57) ABSTRACT

A heart valve prosthesis configured for deployment within a native heart valve. The heart valve prosthesis includes a tubular stent and a prosthetic valve component disposed within and secured to the stent. In addition, at least two positioning elements are coupled to a distal end of the stent to position and anchor the prosthesis within the native heart valve. Each positioning element transforms from a compressed configuration in which the positioning elements distally extend from the distal end of the stent to a deployed configuration in which the positioning elements proximally extend from the distal end of the stent. Each positioning element includes at least one U-shaped or V-shaped support arm that bends radially outward and then towards an outer surface of the stent such that it translates more than ninety degrees from the compressed configuration. Each positioning element may include an outer support arm and an inner support arm.

22 Claims, 17 Drawing Sheets

(56) References Cited

U.S. PATENT DOCUMENTS

| | | |
|---|---|---|
| 2004/0111111 A1 | 6/2004 | Lin |
| 2008/0071361 A1 | 3/2008 | Tuval et al. |
| 2009/0216313 A1 | 8/2009 | Straubinger et al. |
| 2009/0240320 A1 | 9/2009 | Tuval et al. |
| 2009/0276027 A1 | 11/2009 | Glynn |
| 2010/0191320 A1 | 7/2010 | Straubinger et al. |
| 2010/0262231 A1 | 10/2010 | Tuval et al. |
| 2011/0137397 A1 | 6/2011 | Chau et al. |
| 2012/0041550 A1 | 2/2012 | Salahieh et al. |
| 2012/0078360 A1 | 3/2012 | Rafiee |
| 2012/0101572 A1 | 4/2012 | Kovalsky et al. |

FOREIGN PATENT DOCUMENTS

| | | |
|---|---|---|
| WO | WO2012095159 | 7/2012 |
| WO | WO2013/021374 | 2/2013 |
| WO | WO2014028112 | 2/2014 |

OTHER PUBLICATIONS

Lauten et al., "Experimental Evaluation of the JenaClip Transcatheter Aortic Valve" Catheterization and Cardiovascular Interventions 74:514-519 (2009).

Chau, Mark, U.S. Appl. No. 61/287,099, "Prosthetic Mitral Valve With Subvalvular Anchoring" filed Dec. 16, 2009.

Chau et al., U.S. Appl. No. 61/266,774, "Prosthetic Mitral Valve with Subvalvular Anchoring" filed Dec. 4, 2009.

International Search Report and Written Opinion, Int'l Appl. No. PCT/US2013/045789, Dated Dec. 6, 2013.

PCT International Search Report and Written Opinion, PCT/US2014/020876, mailed Jul. 2, 2014.

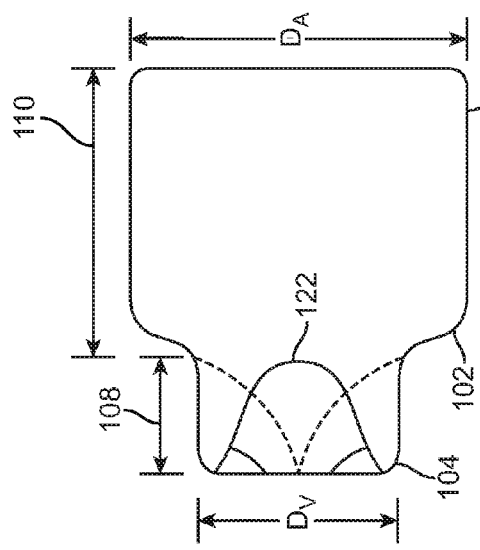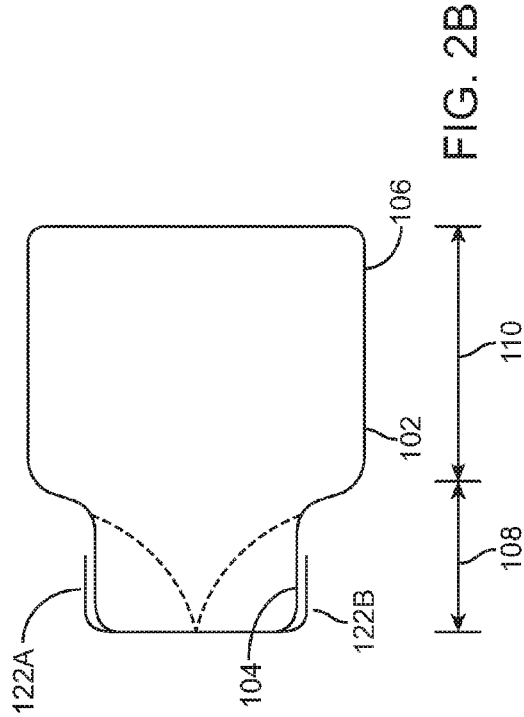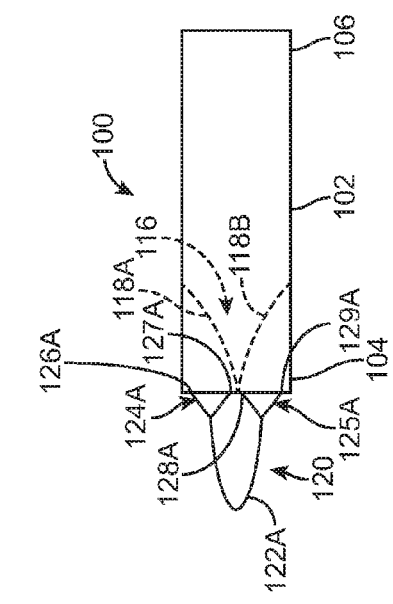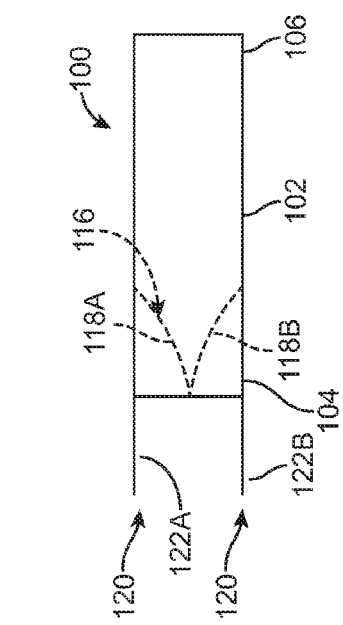
FIG. 1A
FIG. 1B
FIG. 2A
FIG. 2B

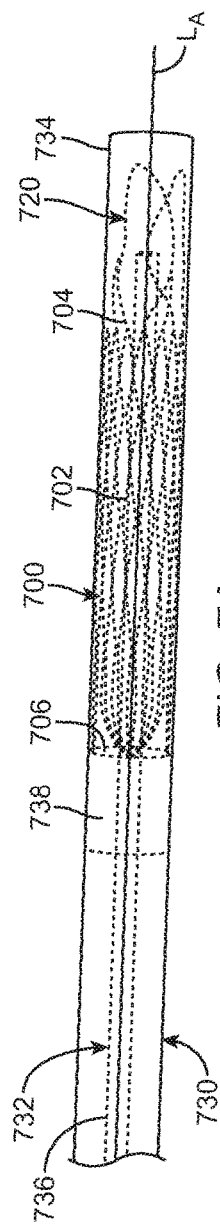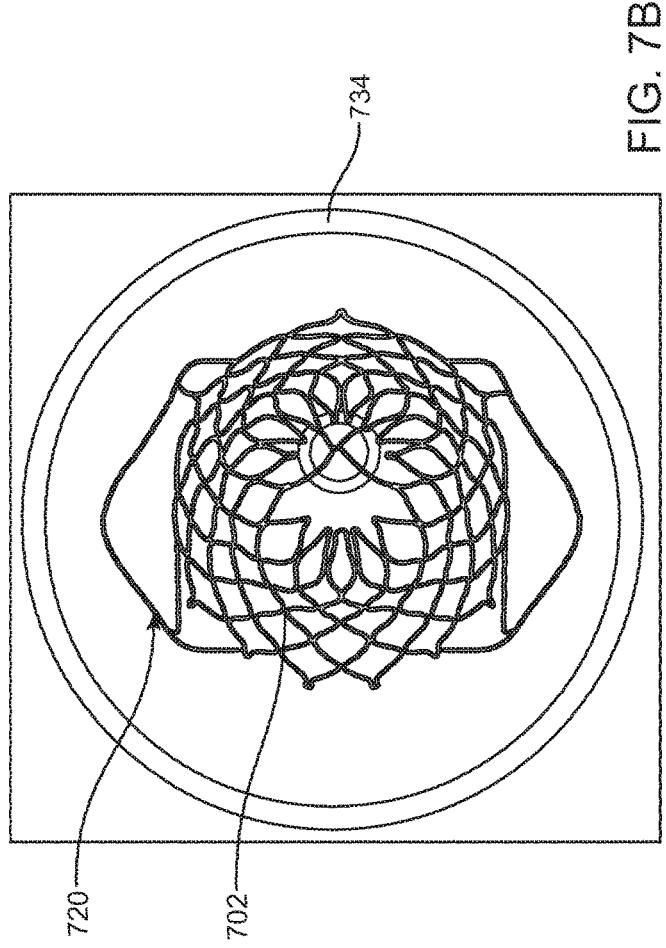

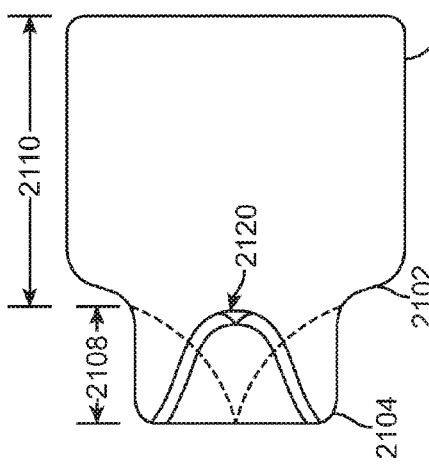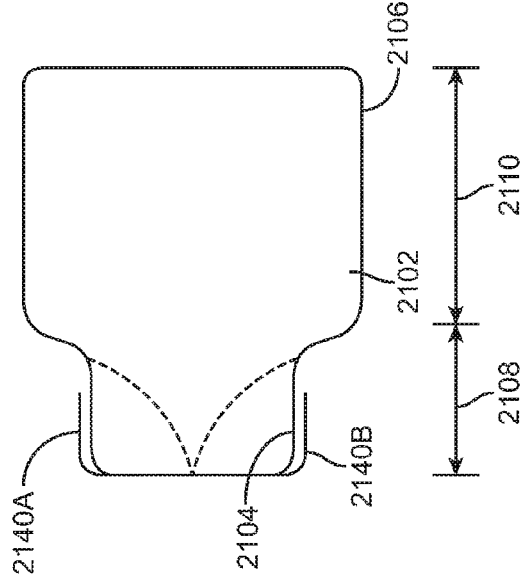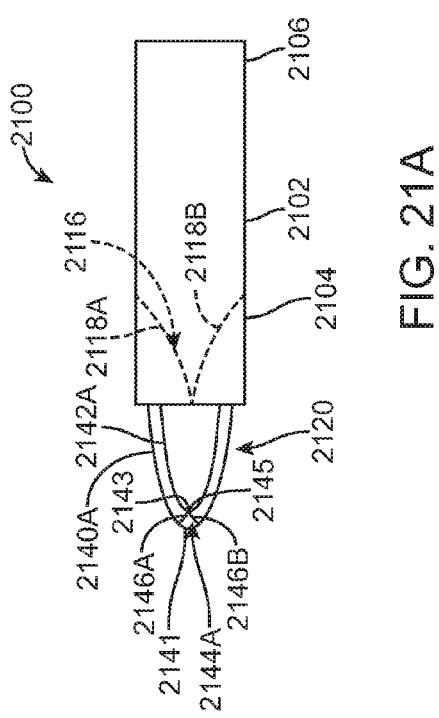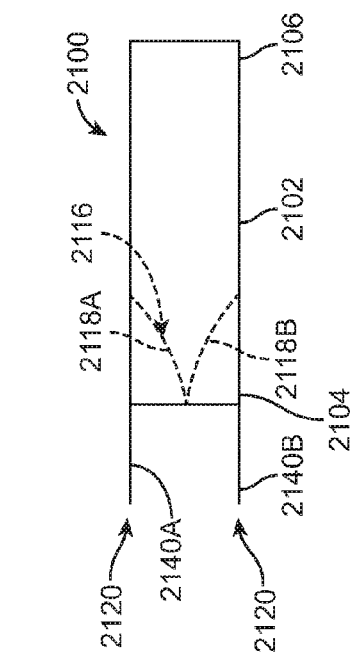
FIG. 21A
FIG. 21B
FIG. 22A
FIG. 22B

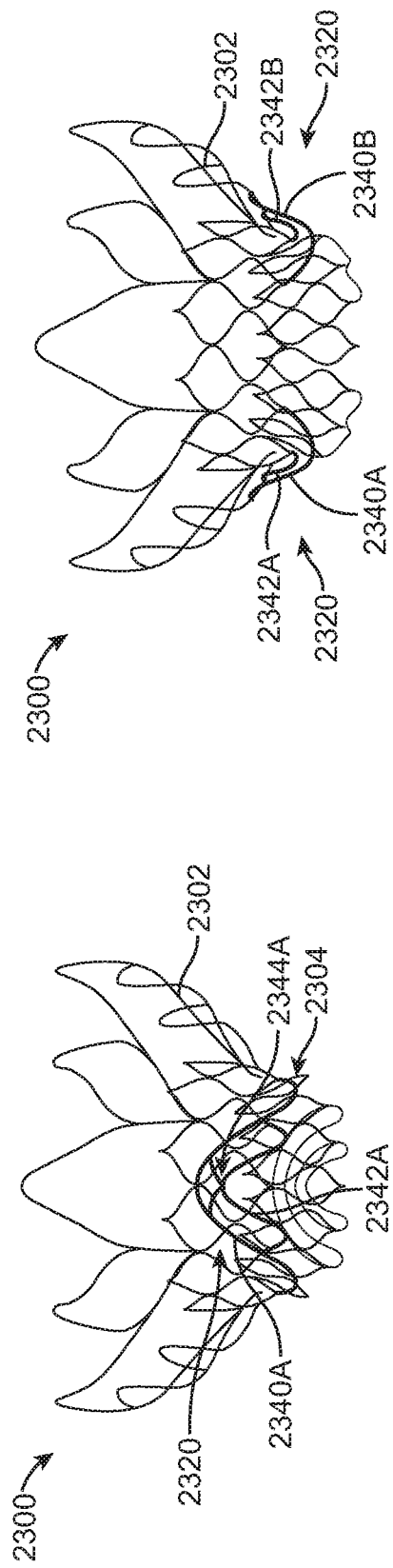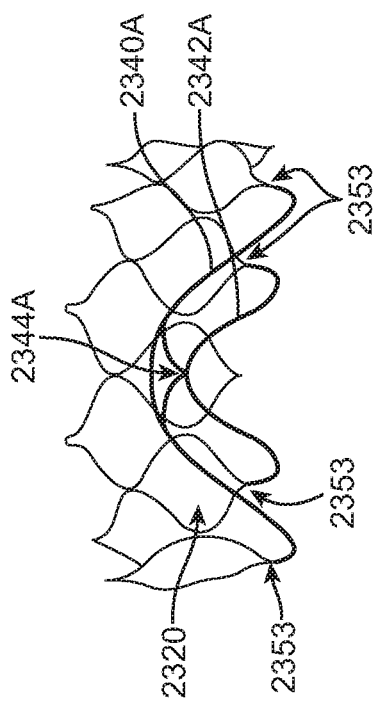
FIG. 23A
FIG. 23B
FIG. 23C

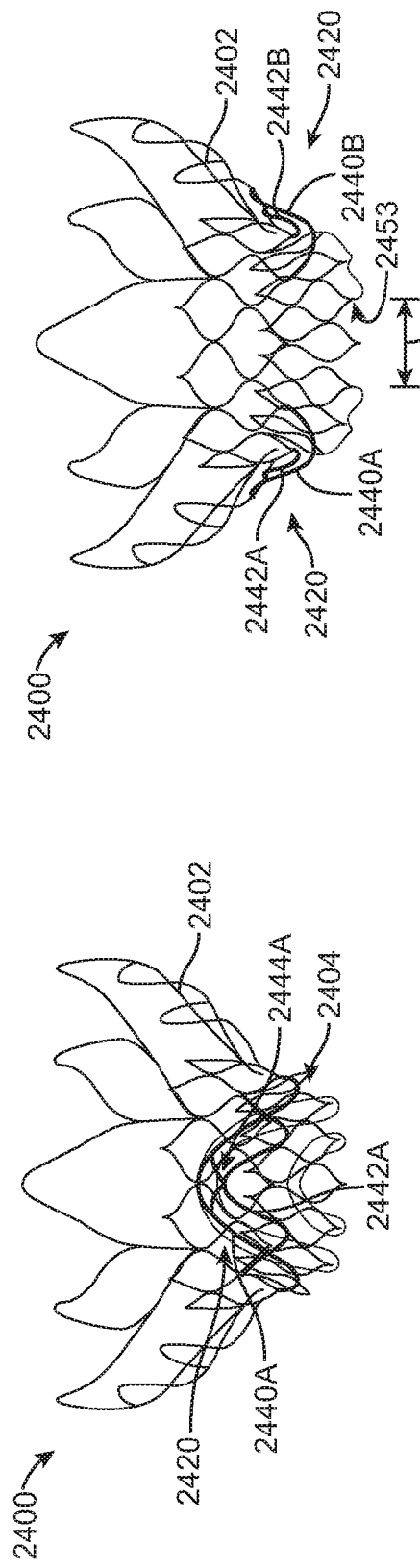
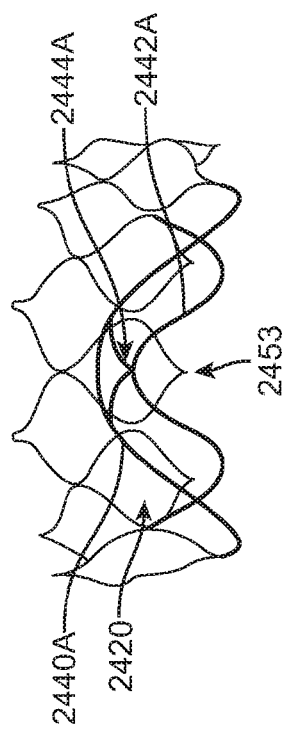
FIG. 24A
FIG. 24B
FIG. 24C

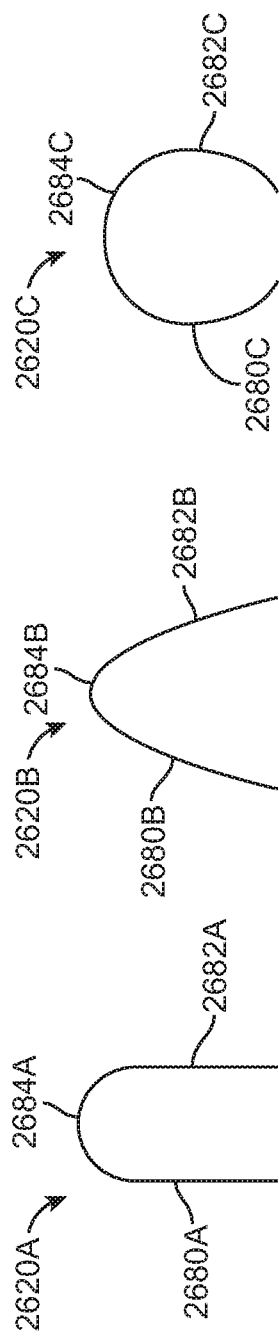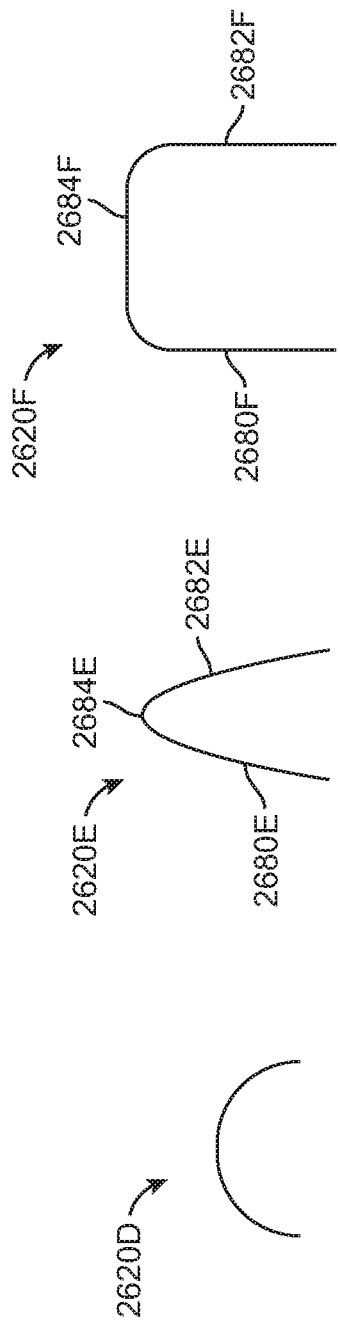

HEART VALVE PROSTHESIS

RELATED APPLICATIONS

This application is a Divisional of U.S. patent application Ser. No. 13/572,842 filed Aug. 13, 2012, now allowed, the disclosures of which is herein incorporated by reference in its entirety.

FIELD OF THE INVENTION

The present invention is directed to a valve prosthesis having positioning elements for positioning and anchoring the prosthesis at a target location and a method of percutaneously delivering the prosthesis to the target location.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, veins gastrointestinal tract, biliary tract, urethra, trachea, hepatic and cerebral shunts, and fallopian tubes. Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower, et al., each of which is incorporated by reference herein in its entirety. Minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state.

A human heart includes two atrio-ventricular valves through which blood flows from the atria to the ventricles, the valves functioning to prevent return of blood to the atrium. The tricuspid valve, also known as the right atrio-ventricular valve, is a tri-flap valve located between the right atrium and the right ventricle. The mitral valve, also known as the bicuspid or left atrioventricular valve, is a dual-flap valve located between the left atrium (LA) and the left ventricle (LV), and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Due to the different physical characteristics of the mitral valve as compared to other valves such as the pulmonary valve, percutaneous implantation of a valve in the mitral position has its own unique requirements for valve replacement. There is a continued desire to improve mitral valve replacement devices and procedures to accommodate the structure of the heart, including by providing improved devices and methods for replacing the mitral valve percutaneously.

BRIEF SUMMARY OF THE INVENTION

Embodiments hereof relate to a heart valve prosthesis that includes a tubular stent and a prosthetic valve component disposed within and secured to the stent. The stent has a compressed configuration for delivery within a vasculature and a deployed configuration for deployment within a native heart valve. In addition, at least two positioning elements are coupled to a distal end of the stent to position and anchor the prosthesis within the native heart valve. Each positioning element includes an outer U-shaped or V-shaped support arm and an inner U-shaped or V-shaped support arm that both distally extend from the distal end of the stent when the stent is in the compressed configuration. During deployment of the prosthesis, each support arm bends radially outward and then towards an outer surface of the stent such that it translates more than ninety degrees from the compressed configuration to proximally extend from the distal end of the stent when the stent is in the deployed configuration.

According to another embodiment hereof, a heart valve prosthesis includes a tubular stent and a prosthetic valve component disposed within and secured to the stent. The stent has a compressed configuration for delivery within a vasculature and a deployed configuration for deployment within a native heart valve. In addition, at least two positioning elements are coupled to a distal end of the stent to position and anchor the prosthesis within the native heart valve. Each positioning element is attached to the stent by two V-shaped connectors such that there are four connection points between each positioning element and the stent. Each positioning element includes a U-shaped or V-shaped support arm that is approximately parallel with a longitudinal axis of the stent and distally extends from the distal end of the stent when the stent is in the compressed configuration. During deployment of the prosthesis, each positioning element bends radially outward and then towards an outer surface of the stent such that the support arm translates between 135 degrees and 180 degrees from the compressed configuration to proximally extend from the distal end of the stent when the stent is in the deployed configuration.

Embodiments hereof also relate to a method of percutaneously delivering and deploying a prosthetic valve within a native mitral valve. A prosthetic valve delivery system is tracked through the vasculature to the native mitral valve. The prosthetic valve delivery system includes a valve prosthesis having a tubular stent, a prosthetic valve component disposed within and secured to the stent, and at least two positioning elements coupled to a distal end of the stent, the two positioning elements each having an outer U-shaped or V-shaped support arm and an inner U-shaped or V-shaped support arm that both distally extend from the distal end of the stent when the stent is in a compressed configuration for delivery. An outer sheath of the prosthetic valve delivery system is retracted to expose the positioning elements, wherein each support arm bends radially outward and then towards an outer surface of the stent such that it translates more than ninety degrees from the compressed configuration to proximally extend from the distal end of the stent and press against the native mitral valve and/or the left ventricular wall in order to position the valve prosthesis. The outer sheath is further retracted to expose the stent, thereby allowing the stent to self-expand into a deployed configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1A and FIG. 1B are schematic side and top views, respectively, of a valve prosthesis having positioning elements according to an embodiment hereof, wherein the valve prosthesis is in a delivery or compressed configuration with positioning elements distally extending from a distal end of the prosthesis.

FIG. 2A and FIG. 2B are schematic side and top views, respectively, of the valve prosthesis of FIG. 1A and FIG. 1B, wherein the valve prosthesis is in an expanded or deployed configuration with positioning elements proximally extending from a distal end of the prosthesis.

FIGS. 7A and 7B illustrate side and end views, respectively, of a valve prosthesis in an unexpanded or delivery or compressed configuration, loaded into a delivery system, according to an embodiment hereof.

FIG. 21A and FIG. 21B are schematic side and top views, respectively, of a valve prosthesis having positioning elements with outer and inner U-shaped support arms according to an embodiment hereof, wherein the valve prosthesis is in a delivery or compressed configuration with positioning elements distally extending from a distal end of the prosthesis.

FIG. 22A and FIG. 22B are schematic side and top views, respectively, of the valve prosthesis of FIG. 21A and FIG. 21B, wherein the valve prosthesis is in an expanded or deployed configuration with positioning elements proximally extending from a distal end of the prosthesis.

FIGS. 23A and 23B illustrate two side views of a valve prosthesis having positioning elements with outer and inner U-shaped support arms according to an embodiment hereof, wherein the support arms extend from distalmost crowns of the valve prosthesis and the valve prosthesis is in an expanded or deployed configuration.

FIG. 23C is an enlarged view of a portion of the valve prosthesis of FIG. 23A.

FIGS. 24A and 24B illustrate two side views of a valve prosthesis having positioning elements with outer and inner U-shaped support arms according to an embodiment hereof, wherein the support arms extend from between the distalmost crowns of the valve prosthesis and the valve prosthesis is in an expanded or deployed configuration.

FIG. 24C is an enlarged view of a portion of the valve prosthesis of FIG. 24A.

FIGS. 26A-26F illustrates various configurations of generally U-shaped or V-shaped support arms according to embodiments hereof.

DETAILED DESCRIPTION OF THE INVENTION

Figure 3:
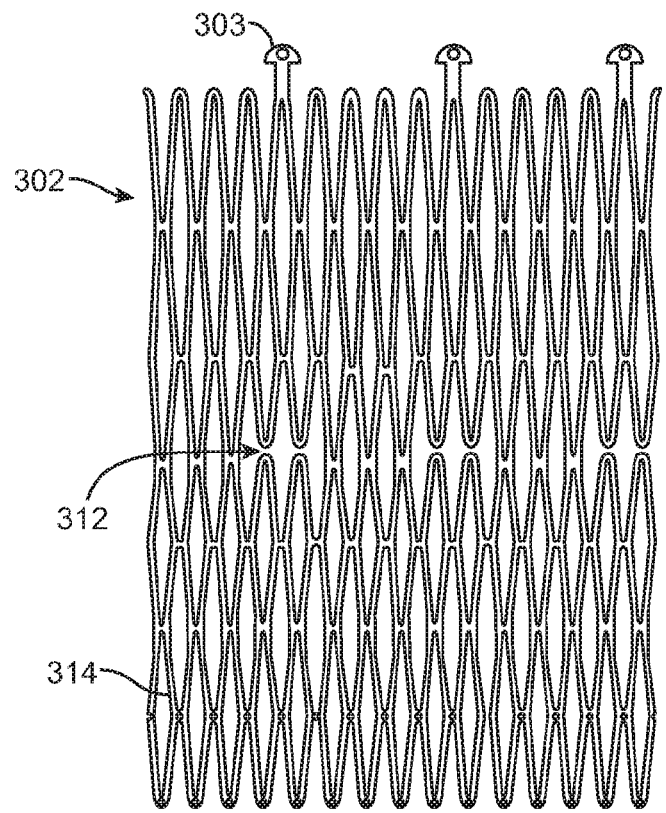
FIG. 3 is a side view illustration of an exemplary stent that may be utilized in the valve prosthesis of FIG. 1A and FIG. 1B, wherein the stent is in a delivery or compressed configuration.
Figure 4:
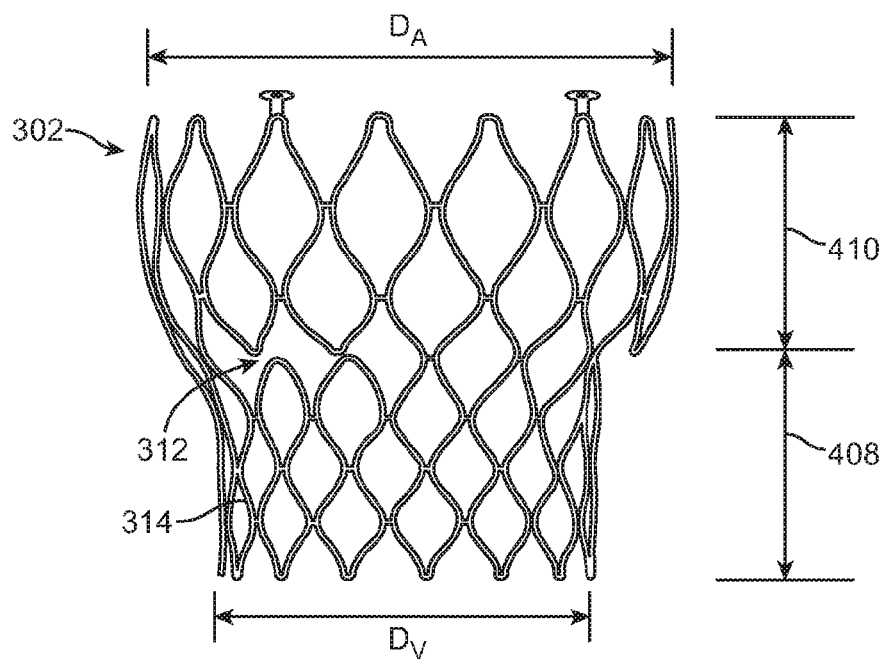
FIG. 4 is a side view illustration of the exemplary stent of FIG. 3, wherein the stent is in an expanded or deployed configuration.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, as used herein, the terms "outward" or "outwardly" refer to a position radially away from a longitudinal axis of the stent and the terms "backward" or "backwardly" refer to the relative transition from a proximal position to a distal position.

The following detailed description is merely exemplary in nature and is not intended to limit the invention or the application and uses of the invention. Although the description of the invention is in the context of treatment of heart valves such as the mitral valve, the invention may also be used in any other body passageways where it is deemed useful. Furthermore, there is no intention to be bound by any expressed or implied theory presented in the preceding technical field, background, brief summary or the following detailed description.

Embodiments hereof are related to a valve prosthesis configured for placement at a mitral valve in the heart that lies between the left atrium (LA) and the left ventricle (LV). More particularly, a valve prosthesis 100 is shown in its compressed or delivery configuration in the side views of FIG. 1A and FIG. 1B and in its expanded or deployed configuration in the side views of FIG. 2A and FIG. 2B. Valve prosthesis 100 includes a framework or stent 102, a valve component 116 attached within the interior portion of stent 102, and at least two positioning elements 120. As will be explained in more detail herein, each positioning element 120 bends or rotates more than ninety degrees with respect to its compressed, delivery configuration during deployment of valve prosthesis 100. In one embodiment, each positioning element 120 rotates between 135 degrees and 180 degrees during deployment of valve prosthesis 100. In the delivery configuration of FIG. 1A and FIG. 1B, each positioning element 120 distally extends from a distal end 104 of stent 102. When released from a delivery sheath (not shown in FIG. 1A or FIG. 1B), each positioning element 120 gradually bends outwardly and then towards an outer surface of the delivery device or stent until it reaches its deployed configuration of FIG. 2A and FIG. 2B in which each positioning element 120 proximally extends from distal end 104 of stent 102. Once deployed, positioning elements 120 function to position and anchor valve prosthesis 100 at a native mitral valve target site. When deployed at a native mitral valve target site, the configuration/structure of a valve prosthesis as well as the delivery system and method of use must accommodate the size of the left ventricle and refrain from obstructing the left ventricular outflow tract By rotating from an initial distally-extending configuration to a final proximally-extending configuration, positioning elements 120 are particularly configured to be deployed within a native mitral valve target site as will be explained in more detail below.

Stent 102 of valve prosthesis 100 is a generally tubular expandable body having a stepped profile extending between a proximal end 106 and distal end 104. As shown in the deployed configuration of FIG. 2A and FIG. 2B, stent 102 includes a distal or ventricular segment 108 having an expanded diameter $D_V$ and a proximal or atrial segment 110 having an expanded diameter $D_A$ which is greater than diameter $D_V$. When placed at a native mitral valve target site, ventricular segment 108 extends into the left ventricle and atrial segment 110 extends into the left atrium. Each segment of stent 102, i.e., ventricular segment 108 and/or atrial segment 110, may be designed with a number of different configurations and sizes to meet the different requirements of the locations in which it may be implanted. Each segment of stent 102, i.e., ventricular segment 108 and/or atrial segment 110, may have the same or different cross-section which may be for example circular, ellipsoidal, rectangular, hexagonal, square, or other polygonal shape, although at present it is believed that circular or ellipsoidal may be preferable when the valve prosthesis is being provided for replacement of the mitral valve.

In embodiments hereof, stent 102 may be made from stainless steel, a pseudo-elastic metal such as a nickel titanium alloy or Nitinol, or a so-called super alloy, which may have a base metal of nickel, cobalt, chromium, or other metal. Stent 102 is self-expanding to return to an expanded deployed state from a compressed or constricted delivery state. "Self-expanding" as used herein means that stent 102 has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. For self-expanding stent structures, one example of a delivery system that can be used includes a catheter with a retractable sheath that covers and compresses the stent and its associated valve structure until it is to be deployed, at which point the sheath can be retracted to allow the stent frame to assume its expanded or deployed configuration. Further details of such a delivery process for delivering stented valve prostheses as described herein are discussed in further detail below.

Figure 5:
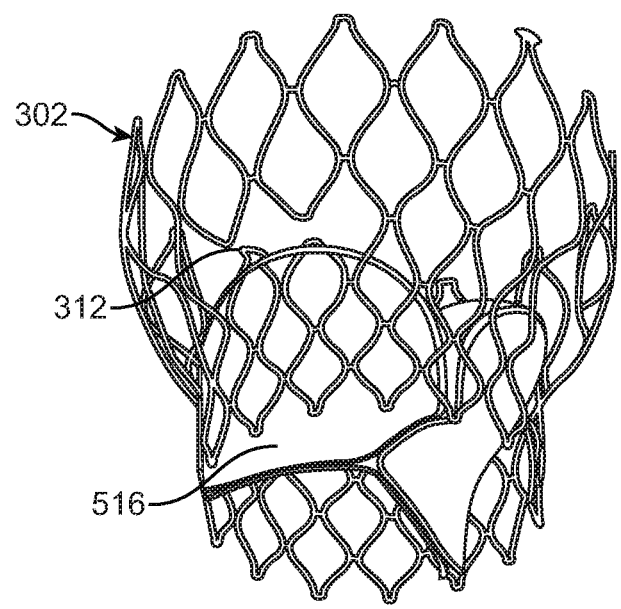
FIG. 5 is an isometric view illustration of the exemplary stent of FIG. 3, wherein the stent is in an expanded or deployed configuration and includes a prosthetic valve located therein.
Figure 6:
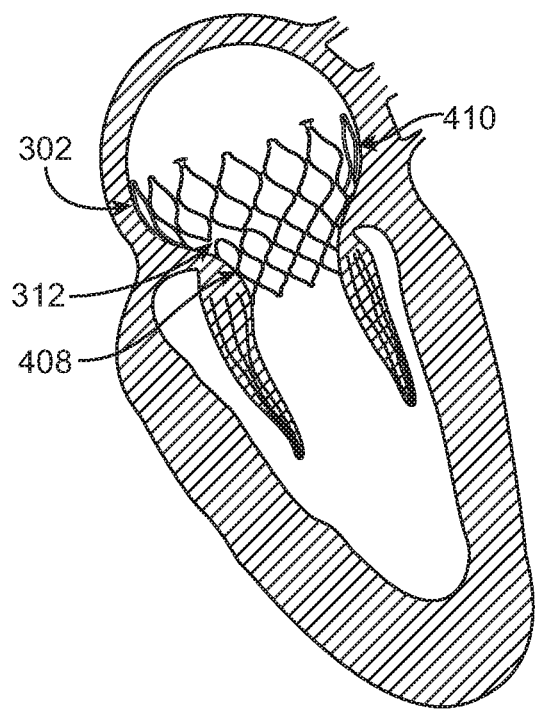
FIG. 6 is a side view illustration of the exemplary stent of FIG. 3, wherein the stent is in an expanded or deployed configuration and positioned within at a mitral valve of a heart.

As shown in FIGS. 3-6, stent 302 has a lattice configuration 314, with connectors 303 extending from an end of stent 302 for connecting to a delivery system (not shown). Stent 302 is shown in a compressed configuration and deployed configuration in FIG. 3 and FIG. 4, respectively. Similar to stent 102, stent 302 includes an expandable body having a stepped outer diameter formed by a distal or ventricular segment 408 having an expanded diameter $D_V$ and a proximal or atrial segment 410 having an expanded diameter $D_A$ which is greater than diameter $D_V$. Stent 302 is shown deployed at a native mitral valve target site in FIG. 6, with ventricular segment 408 extending into the left ventricle and atrial segment 410 extending into the left atrium. Stent 302 is a unitary integral structure formed from a single tubular component. Lattice configuration 314 of stent 302 may be produced by machining or laser cutting the stent from a metal tube, as is commonly employed in the manufacturing of stents. Lattice configuration 314 includes disconnected or decoupled turns or crowns 312 at the transition area between ventricular segment 408 and atrial segment 410, which advantageously allows leaflets of a valve component 516 to extend into atrial segment 410 (and into the left atrium when in situ) as shown in FIG. 5 rather than be solely located on the outflow or ventricular segment 408 of stent 302 (and into the left ventricle in situ). By locating a portion of the valve leaflets in the left atrium, the required length of ventricular segment 408 is minimized and the length of the stent that protrudes into the left ventricle may be reduced. Further description of stent 302 and advantages thereof are described in co-pending patent application, U.S. application Ser. No. 13/278,050 filed Oct. 20, 2011.

Although stent 102 is shown with a lattice configuration, it will be understood by those of ordinary skill in the art that the body of stent 102 may have any configuration or pattern suitable for placement at a native mitral valve target site.

As mentioned above, a stent of valve prosthesis 300 may be laser cut from a solid component of self-expanding material such that the stent is an integral structure that does not include individual components. A single integral structure allows the stent to be crimped or compressed to a low delivery profile. Alternatively, rather than being laser cut, the stent may be formed using any of a number of different methods that would be apparent to one of ordinary skill in the art such as connecting individual annular stent struts together, chemical etching, or another method of cutting a desired shape from a solid component.

Referring back to FIGS. 1A, 1B, 2A, and 2B, valve prosthesis 100 includes prosthetic valve component 116 within the interior of stent 102 which is capable of blocking flow in one direction to regulate flow there through. Prosthetic valve component 116 includes valve leaflets constructed of pericardium material and may form a bicuspid, tricuspid, or tubular replacement valve. FIG. 1A, FIG. 1B, FIG. 2A, and FIG. 2B illustrate an exemplary bicuspid valve having two leaflets 118A, 118B, although a tricuspid leaflet configuration may alternatively be used in embodiments hereof.

Valve leaflets 118A, 118B are sutured or otherwise securely and sealingly attached to the interior surface of stent 102 and/or graft material (not shown) enclosing or lining stent 102 as would be known to one of ordinary skill in the art of prosthetic tissue valve construction. The graft material may be a low-porosity woven fabric, such as polyester, Dacron fabric, or PTFE, which creates a one-way fluid passage when attached to the stent. In one embodiment, the graft material may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material could also be a natural material such as pericardium or another membranous tissue such as intestinal submucosa.

As described above, leaflets 118A, 118B may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 118A, 118B include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Positioning elements 120 will now be described in more detail. Referring also to FIG. 26A, positioning elements 120 are generally shown in the figures as being a wire or tubular structure formed into a U-shaped or generally U-shaped configuration such that each positioning element has two straight side segments 2680A, 2682A with a bottom curved segment 2684A. As will be understood by those of ordinary skill in the art, "side" and "bottom" are relative terms and utilized herein for illustration purposes only. The straight side segments may be parallel to each other as shown in FIG. 26A, or may be slanted or angled away from each other as shown in FIG. 26B in which two straight slanted side segments 2680B, 2682B flare apart as they extend from bottom curved segment 2684B. As utilized herein, "generally" U-shaped includes wire or tubular structures formed into: a horseshoe shape as shown in FIG. 26C in which two curved side segments 2680C, 2682C have ends that converge together as they extend from bottom curved segment 2684C; a semi-circle 2620D as shown in FIG. 26D; and an oblong shape 2620F as shown in FIG. 26F in which two parallel straight side segments 2680F, 2682F have a straight bottom segment 2684F therebetween. In another embodiment hereof, the positioning elements may be generally V-shaped as shown in FIG. 26E in which two straight slanted side segments 2680C, 2682C are connected together by a curved apex 2684E. The positioning elements may be considerably longer, shorter, wider, or narrower than shown. In any case, the positioning elements are preferably configured to be a shape and size that can provide a positioning function and an anchoring function for valve prosthesis 100 when the prosthesis is deployed at a native valve target site. For example, if valve prosthesis 100 is positioned within the native mitral valve annulus, the positioning elements extend from stent 102 on the ventricular or outflow side of the mitral valve and provide interference with the native valve leaflets and/or the walls of the left ventricle, thereby inhibiting motion of valve prosthesis 100.

Each positioning element 120 rotates and transforms from the distally-extending compressed configuration to proximally-extending deployed configuration. FIG. 7A and FIG. 7B illustrate side and end views, respectively, of a valve prosthesis 700 in an compressed or delivery configuration sized for delivery to the target site, loaded into a delivery system 730. Valve prosthesis 700 includes a tubular frame or stent 702 which is similar to stent 302 described above, a valve (not shown in FIGS. 7-13 for illustrative purposes) attached within the interior portion of stent 702, and two positioning elements 720. In the compressed or delivery configuration, each positioning element 720 is approximately parallel with a longitudinal axis $L_a$ of stent 702 and distally extends from a distal end 704 of stent 702. Delivery system 730 includes a catheter 732 and an outer retractable sheath or tube 734. Valve prosthesis 700 is mounted over an inner shaft 736 of catheter 732 at the distal end thereof and sheath 734 surrounds and constrains valve prosthesis 700 in the compressed configuration. In one embodiment, catheter 732 may also include a retainer 738 which temporarily secures proximal end 706 of stent 702 onto catheter 732. For example, retainer 738 may include an end stent capture configuration as described in U.S. Patent Pub. 2009/0276027 to Glynn, which is hereby incorporated by reference herein in its entirety.

Figure 8:
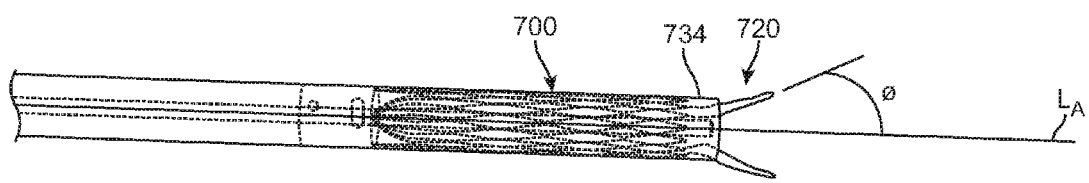
FIGS. 8-10 illustrate side views of the valve prosthesis of FIG. 7, wherein a sheath of the delivery system is progressively retracted to expose the positioning elements of the valve prosthesis.

In order to begin deployment of valve prosthesis 700, sheath 734 is retracted in a proximal direction to expose and release positioning elements 720 as shown in FIG. 8. Upon initial release from sheath 734, positioning elements 720 flare or spread outwardly from the distal end of stent 702 such that positioning elements 720 form an acute angle θ with respect to longitudinal axis $L_a$.

Figure 9:
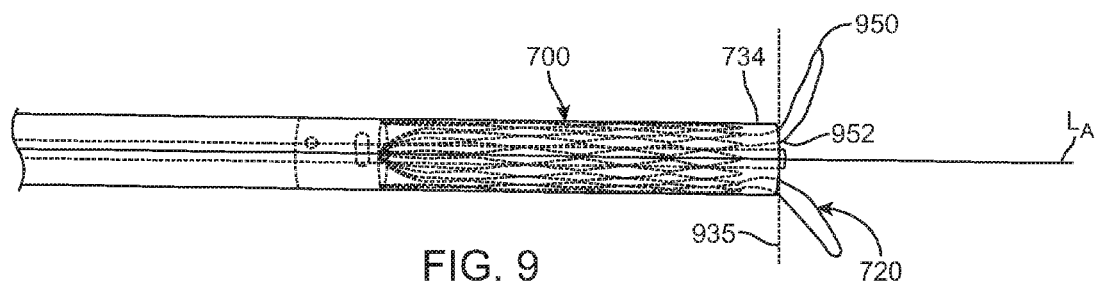
Figure 10:
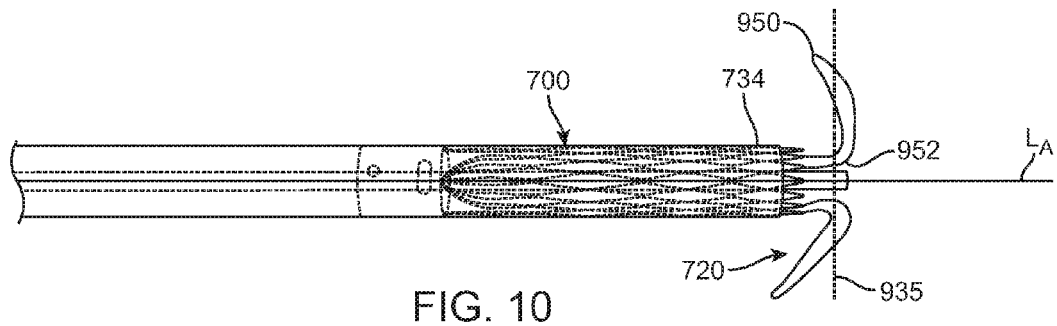

As sheath 734 is further retracted, positioning elements 720 continue to be exposed and continue to bend backwards towards the outer surface of sheath 734 and stent 702. Notably, as positioning elements 720 are released from sheath 734, stent 702 remains constrained within sheath 734. FIG. 9 illustrates positioning elements 720 approaching a transverse reference axis 935 between the initial distally-extending compressed configuration and the final proximally-extending deployed configuration. Transverse reference axis 935 as utilized herein describes an imaginary reference line that extends approximately ninety degrees or perpendicular to the longitudinal axis La of stent 702. FIG. 10 illustrates positioning elements 720 after passing over the transverse reference axis 935, with positioning elements 720 fully exposed or released from sheath 734 while stent 702 is still compressed within sheath 734. One particular feature of positioning elements 720 is apparent when comparing FIG. 9 and FIG. 10. Positioning elements 720 bend or curve gradually backwards such that distal portions or tips 950 of positioning elements 720 pass over the transverse reference axis 935 before proximal portions or bases 952 of positioning elements 720. After distal tips 950 of positioning elements 720 pass or cross over the transverse reference axis 935 and are pointing in a proximal direction, proximal bases 952 of positioning elements 720 approach the transverse reference axis 935 as shown in FIG. 10. Stated another way, distal tips 950 of each positioning element 720 bend past transverse reference axis 935 prior to proximal bases 952 of each positioning element 720. Due to the above-described flaring or expanding sequence in which positioning elements 720 curve backward, the length of positioning elements 720 may be greater than if both the proximal and distal portions of the positioning elements crossed over the transverse reference axis 935 at the same time, i.e., if the positioning elements were straight and extended generally parallel to the transverse reference axis 935 during deployment. In addition, since stent 702 is still compressed within sheath 734, it can be observed that the length of positioning elements 720 may be greater than if stent 702 was released from sheath 734 and in a deployed configuration. Accordingly, the length of positioning elements 720 is maximized which increases their ability to anchor valve prosthesis 700 when it is positioned to replace a valve. In one embodiment in which valve prosthesis 700 is positioned at a mitral valve, the length of each positioning element 720 is between 10 and 12 mm.

Figure 13:
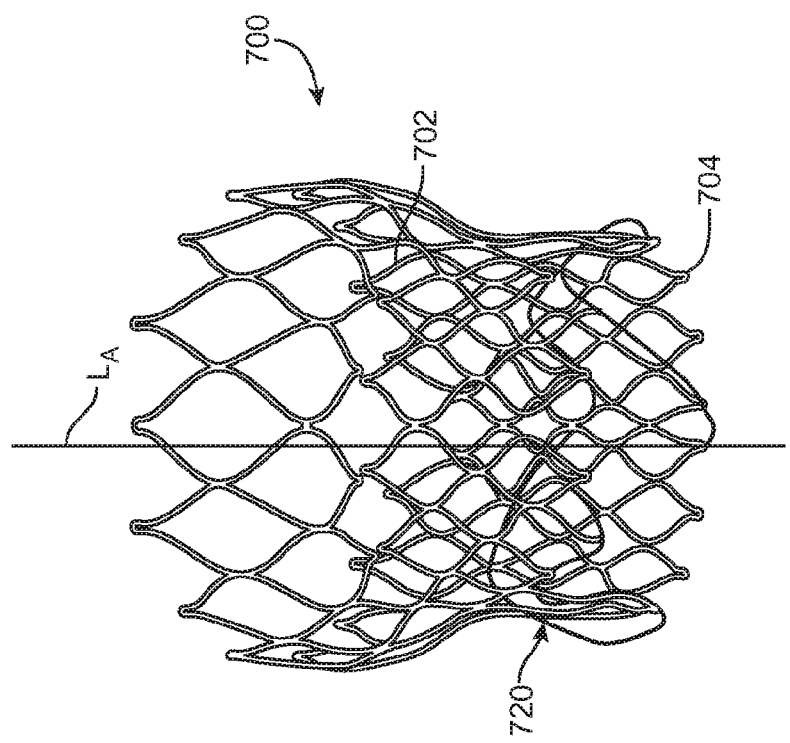
FIG. 13 illustrates a side view of the valve prosthesis of FIG. 7 in an expanded or deployed configuration, after release from the delivery system.
Figure 11:
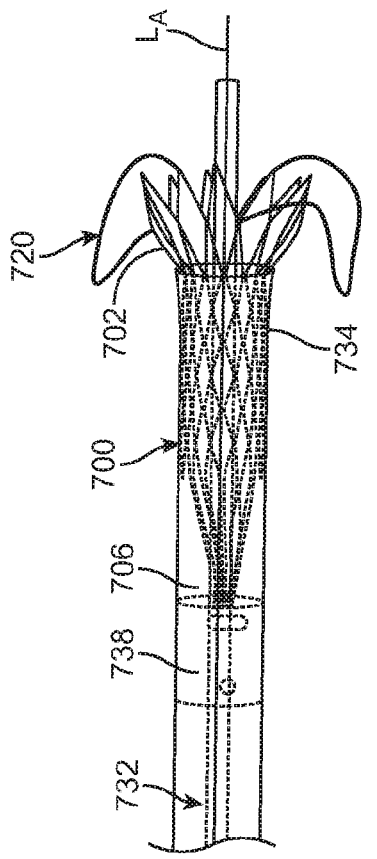
FIGS. 11-12 illustrate side views of the valve prosthesis of FIG. 7, wherein a sheath of the delivery system is progressively retracted to expose the stent of the valve prosthesis.
Figure 12:
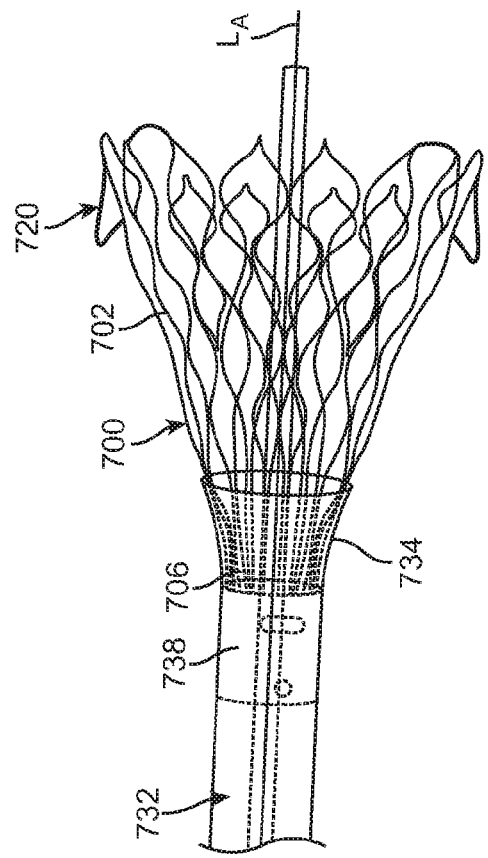

FIG. 11 and FIG. 12 illustrate the continued deployment of valve prosthesis 700. Sheath 734 continues to be proximally retracted, exposing self-expanding stent 702 such that stent 702 is released to assume its deployed configuration. Sheath 734 is proximally retracted until proximal end 706 of stent 702 is exposed and allowed to self-expand, thereby uncoupling from retaining tip 738 of catheter 732. FIG. 13 illustrates the final deployed configuration of valve prosthesis 700, in which each positioning element 720 proximally extends from a distal end 704 of stent 702. As previously described, the backwards rotation that occurs during deployment results in each positioning element 720 translating more than ninety degrees from its compressed, delivery configuration. During deployment, each positioning element 720 essentially deploys or translates in an arc path that extends between 90 and 180 degrees from the initial compressed configuration and the final deployed configuration. In the embodiment of FIG. 13 shown ex vivo, each positioning element 720 bent or rotated approximately 180 degrees between the initial distally-extending compressed configuration and the final proximally-extending deployed configuration. However, when positioned in vivo, tissue such as native valve leaflets may be sandwiched between each positioning element 720 and the outer surface of stent 702 and as a result, the total rotation or bending of positioning elements 720 in the final deployed configuration may be less than 180 degrees with respect to the initial distally-extending compressed configuration.

Rotating from the initial distally-extending configuration to the final proximally-extending configuration allows valve prosthesis 700 to be deployed in the annulus of the native mitral valve rather than the outflow side of the native mitral valve, thereby minimizing the length which the prosthesis and the delivery system protrudes into the left ventricle. More particularly, prior art approaches for delivering a valve prosthesis include initially loading positioning or anchoring elements into the delivery system as proximally-extending, such that the positioning elements are pressed against the stent of the valve prosthesis. Such initially proximally-extending positioning elements flare outward or away from the stent less than ninety degrees when released from a delivery sheath to a final deployed configuration. In order to properly position positioning elements that initially extend in a proximal direction at a mitral valve location, the valve prosthesis would need to be distally extended past the native mitral valve and into the left ventricle prior to retraction of the delivery sheath in order to provide ample space for the positioning elements to deploy. After the positioning elements flared to the acutely angled deployed configuration, the prosthesis would be proximally retracted in order to bring the positioning elements into contact with the native mitral valve. However, in embodiments hereof, since positioning elements are initially loaded into delivery system 730 as distally-extending, valve prosthesis 700 is initially positioned in the annulus of the native mitral valve with only distally-extending positioning elements 720 extending into the left ventricle prior to retraction of the delivery sheath.

In addition, the fact that positioning elements 720 are deployable via one delivery sheath helps accommodate deployment of valve prosthesis 700 at a native mitral valve despite constraints or considerations of delivering a prosthesis in a left ventricle. In some aortic valve applications, multiple tubes are utilized for deploying stented cardiac valve prosthetics. For example, the ENGAGER device from Medtronic, Inc. of Minneapolis, Minn. is a stented cardiac valve prosthesis having positioning elements in which two tubes are utilized for deployment. A first distal cone or tube is distally advanced into the aorta during deployment to deploy the positioning elements and then a second proximal sleeve is proximally retracted to deploy stent frame. However, when deploying a valve prosthesis at a mitral valve target location, distally advancing a tube or sheath into the left ventricle may damage chordae tendineane located within the heart and/or may obstruct the left ventricular outflow tract (LVOT). In addition, the mitral valve is positioned lower in the heart than the aortic valve and thus there is not as much depth/length to distally advance a tube or sheath into the left ventricle. Accordingly, valve prosthesis 700 is deployed via delivery system 730 that includes only one delivery sheath 734 which is proximally retracted.

In order to transform between the initial distally-extending compressed configuration and the final proximally-extending deployed configuration, positioning elements according to embodiments described herein are formed from a self-expanding material that has a mechanical memory to return to the proximally-extending deployed configuration.

For example, the positioning elements may be made from stainless steel, a pseudo-elastic metal such as a nickel titanium alloy or Nitinol, or a so-called super alloy, which may have a base metal of nickel, cobalt, chromium, or other metal. As described above with respect to stent 102, mechanical memory may be imparted to the wire or tubular structure that forms the positioning elements by thermal treatment to achieve a spring temper in stainless steel, for example, or to set a shape memory in a susceptible metal alloy, such as nitinol, or a polymer.

As previously described, each positioning element is coupled to the distal end of the valve prosthesis. In one embodiment, each positioning element may be coupled to the stent at multiple connection points. More specifically referring to FIG. 1A, U-shaped support arm 122A is coupled to distal end 104 of stent 102 via two V-shaped connectors 124A, 125A such that four connection points 126A, 127A, 128A, 129A are located between each positioning element 120 and stent 102. Similarly, shown in the view of FIG. 14, U-shaped support arm 122B is coupled to distal end 104 of stent 102 via two V-shaped connectors 124B, 125B such that four connection points 126B, 127B, 128B, 129B are located between each positioning element 120 and stent 102. In one embodiment, the eight connection points 126A, 127A, 128A, 129A, 126B, 127B, 128B, 129B are approximately equally spaced around the perimeter of distal end 104 of stent 102 and collectively function to prevent the prosthetic valve leaflets from obstructing the outflow end of valve prosthesis 100 and the left ventricular outflow tract (LVOT). Stated another way, V-shaped connectors 124A, 125A, 124B, 125B increase the number of connection points between each support arm 120A, 120B, respectively, and stent 102, and thereby shorten or minimize the open space or distance between adjacent connection points. V-shaped connectors 124A, 125A, 124B, 125B act as an obstacle in the path that the prosthetic valve leaflets would follow when overlapping onto stent 102 and thereby keeps the flow path clear. Although described as "V-shaped connectors," it will be apparent to those of ordinary skill in the art that two straight components formed generally in the shape of a "V" may be utilized in embodiments hereof rather than one single V-shaped component. In addition, although described with respect to positioning elements 120 and stent 102, such connectors may be utilized for forming multiple connection points between any embodiment described herein, including positioning elements 320 and stent 302, and position elements 720 and stent 702.

In one embodiment, positioning elements 120 and stent 102 are formed as an integral unitary structure, such as by laser cutting or etching the positioning elements and stent from a single hollow tube or sheet. In another embodiment, V-shaped connectors 124A, 124B and/or U-shaped support arms 122A, 122B, may be separate components that are formed separately and mechanically coupled to each other and to stent 102 via any suitable mechanical method, including welding, soldering, or by another mechanical method.

Figure 15:
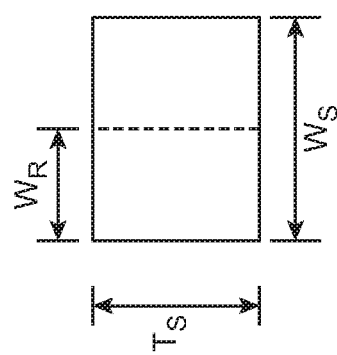
FIG. 15 is a cross-sectional view taken along line X-X of FIG. 14.
Figure 14:
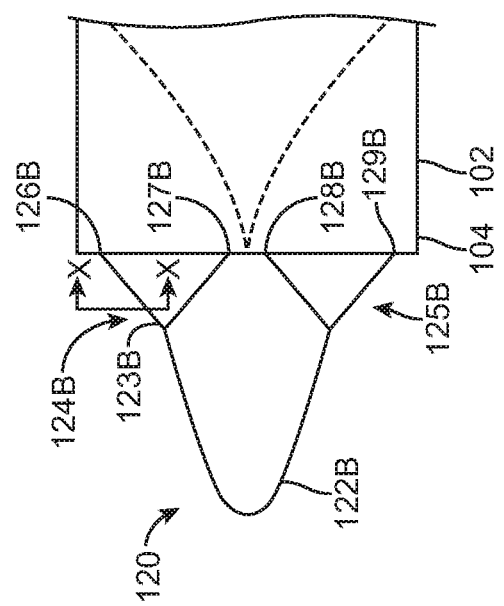
FIG. 14 is a side-view illustration of a portion of the valve prosthesis of FIG. 1, wherein each positioning element is coupled to the stent at four connection points.

In order to lower the amount of stress and/or strain that occurs in V-shaped connectors 124A, 125A, 124B, 125B as positioning elements 120 transform between the initial distally-extending compressed configuration and the final proximally-extending deployed configuration, the width of the wire(s) or tubular member(s) which form V-shaped connectors 124A, 125A, 124B, 125B may be increased as compared to the width or dimension of U-shaped support arms 122A, 122B as well as compared to the width or dimension of the wire or tubular member which forms stent 102. More particularly, FIG. 15 illustrates a sectional view along line X-X of FIG. 14 showing a strut 123B of V-shaped connector 124B according to one embodiment hereof. A reference width $W_R$ is shown in phantom in FIG. 15 and represents the width of the wire or tubular member which forms stent 102 and/or U-shaped support arms 122A, 122B. A width $W_S$ of strut 123B is widened or increased relative to width $W_R$, thereby increasing the amount of material of V-shaped connector 124B such that it can handle the deformation that occurs thereto during deployment of valve prosthesis 100. In order to widen or increase the width of strut 123B, material may be added or banded to strut 123B around the width direction thereof. In an embodiment, material may be added to include the width of strut 123B up to three times of width $W_R$. Preferably, a thickness $T_S$ of strut 123B is not increased relative to the thickness of the wire or tubular member which forms stent 102 due to size constraints on the compressed outer diameter or profile of valve prosthesis 100 when in the compressed configuration. As utilized herein, thickness $T_S$ of strut 123B refers to the strut material that extends in a radial direction relative to stent 102. Although illustrated as constant or uniform, thickness $T_S$ of strut 123B may vary or increase from an inner surface relative to an outer surface of strut 123B.

Figure 16:
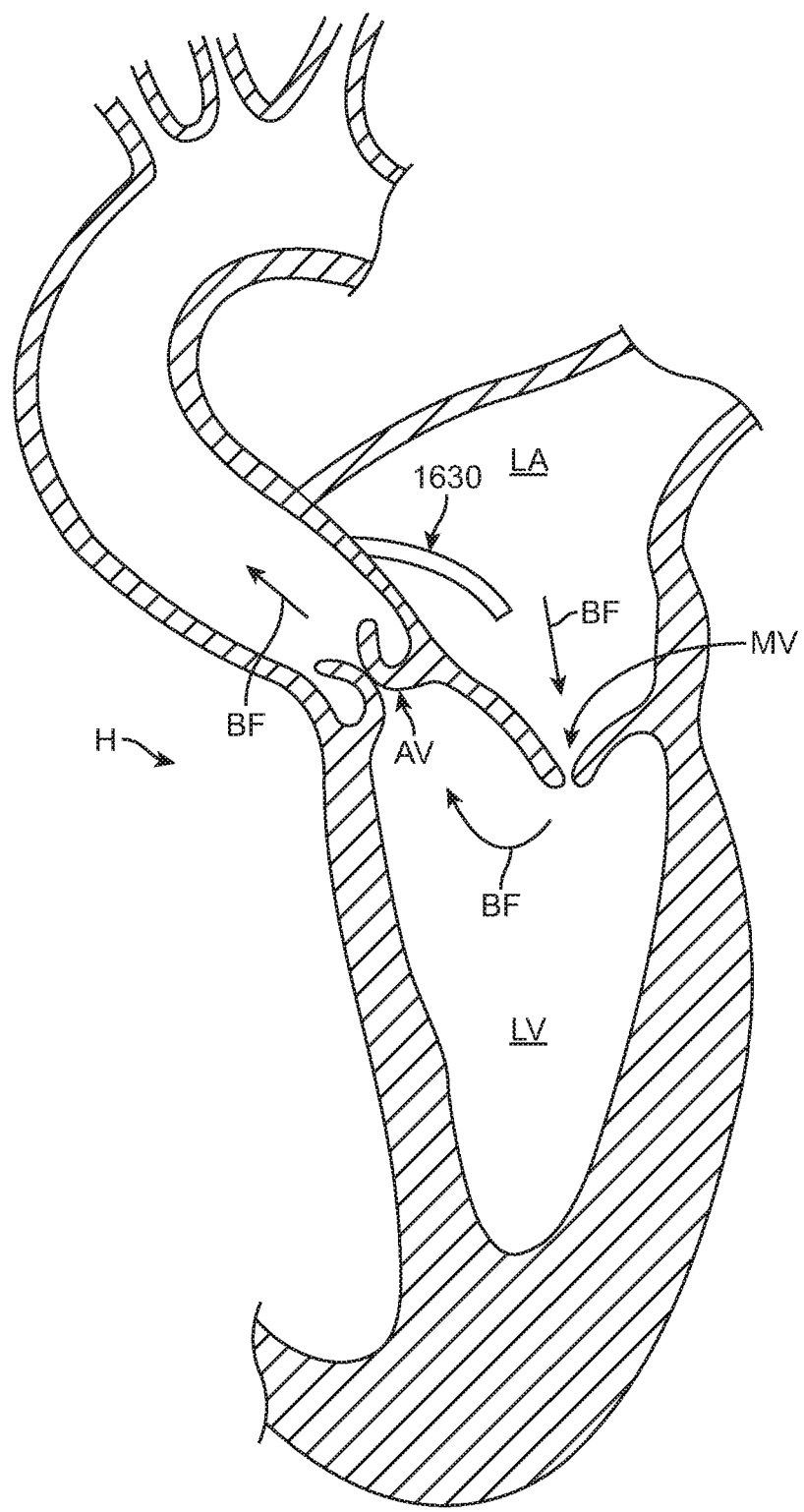
FIG. 16 through FIG. 20 illustrates a method of implanting a valve prosthesis at a mitral valve target location within a heart, according to an embodiment hereof.

FIGS. 16-20 illustrate a method of delivering and implanting stent mitral valve prosthesis 100 in accordance with an embodiment hereof to perform a heart valve replacement procedure, more particularly a mitral valve replacement, with minimal blood flow stoppage or interruption. FIG. 16 illustrates a portion of a heart H including a left atrium LA, a left ventricle LV, a mitral valve space MV and an aortic valve AV. Blood flow BF is depicted with directional arrows in FIG. 16 in the left atrium LA, into left ventricle LV through mitral valve space MV, and into the aorta through aortic valve AV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. However, a valve prosthesis in accordance with an embodiment hereof can be positioned in the area of mitral valve MV when it is not functioning properly (to replace the mitral valve) in accordance with the invention, thereby pushing the native leaflets out of the mitral valve space.

With reference to FIG. 16, a prosthetic valve delivery system 1630 is shown after having been introduced into the vasculature via a percutaneous entry point, a.k.a the Seldinger technique, and having been tracked through the vasculature and into the left atrium so that distal tip 1640 is positioned proximate the mitral valve. For example, the percutaneous entry point may be formed in a femoral vein. Thereafter, a guidewire (not shown) is advanced through the circulatory system, eventually arriving at the heart. The guidewire is directed into the right atrium, traverses the right atrium and is made to puncture with the aid of a transeptal needle or pre-existing hole, the atrial septum, thereby entering the left atrium. Once the guidewire is positioned, the endoluminal entry port and the atrial septum are dilated to permit entry of a guide catheter (not shown) and/or prosthetic valve delivery system 1630 into the left atrium. Thereafter, prosthetic valve delivery system 1630 is advanced into the left atrium through the punctured atrial septum and positioned proximate to the mitral valve MV. Although not shown, it will be understood by those of ordinary skill in the art that prosthetic valve delivery system 1630 may be inserted into a guide catheter in order to be advanced to a position proximate to the mitral valve MV. In addition, although described as a transfemoral antegrade approach for percutaneously accessing the mitral valve, the valve prosthesis 100 may be positioned within the desired area of the heart via entry other different methods such as a transseptal antegrade approach via a thoracotomy for accessing the mitral valve.

Figure 17:
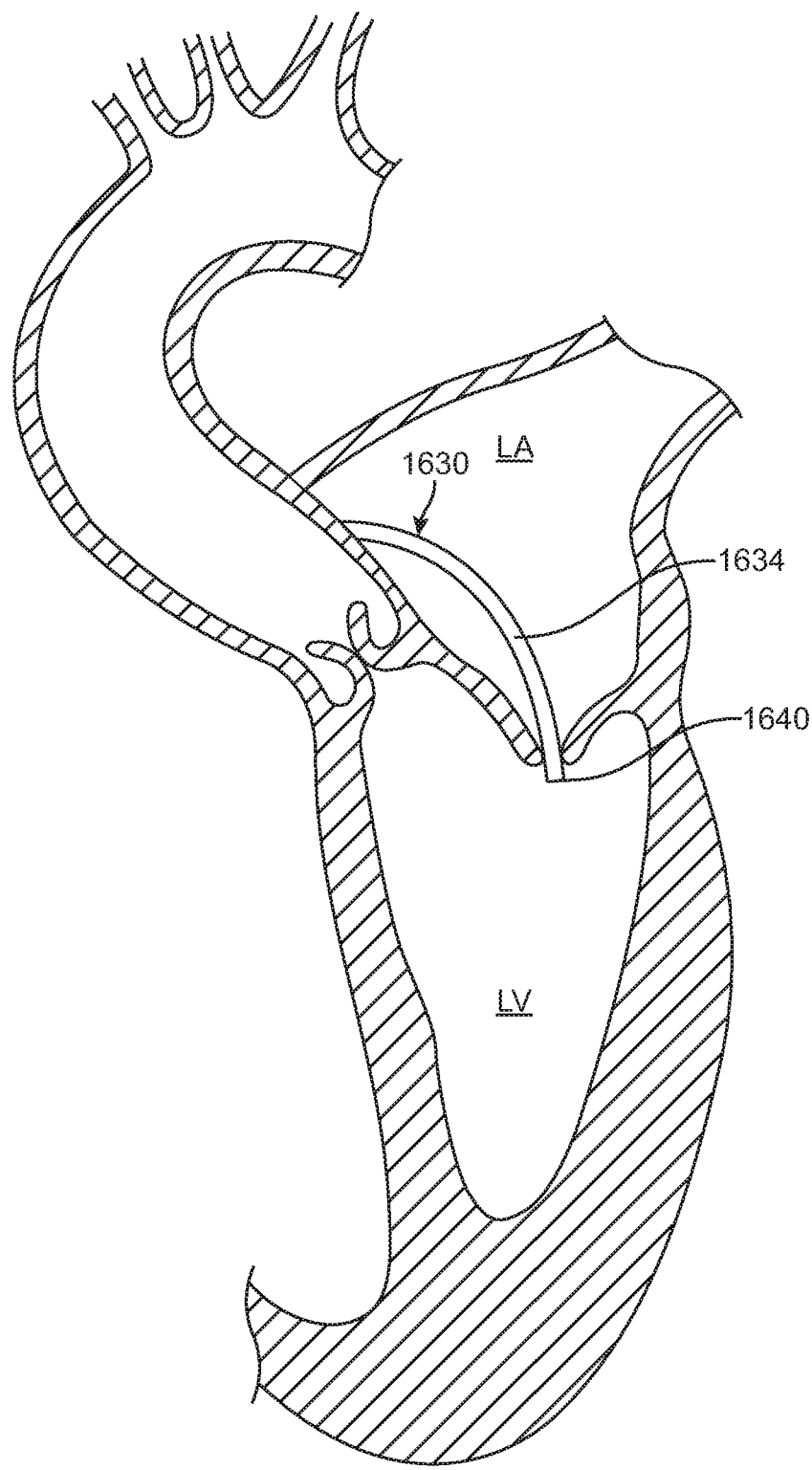

Similar to delivery system 730 described above with respect to FIGS. 7A, 7B and 8-13, prosthetic valve delivery system 1630 includes an outer retractable sheath or tube 1634 positioned over the a catheter (not shown in FIGS. 16-20) having compressed valve prosthesis 100 to keep it from expanding and to minimize interference between the valve prosthesis and the vasculature through which it will be traveling. Valve prosthesis 100 is mounted over an inner shaft of the catheter at the distal end thereof and sheath 1634 surrounds and constrains valve prosthesis 100 in the compressed configuration. After being advanced into the left atrium LA, prosthetic valve delivery system 1630 including sheath 1634 may then be advanced through the mitral valve MV and into the left ventricle LV as shown in FIG. 17. Distal tip 1640 of prosthetic valve delivery system 1630 is advanced into the left ventricle LV until valve prosthesis 100 is centered at the native mitral valve, i.e., deployed in the annulus of the native mitral valve, with positioning elements 120 of valve prosthesis 100 contained within sheath 1634 and distally extending into the left ventricle LV. As previously discussed, deploying valve prosthesis 100 in the middle of the native valve rather than the outflow side of the native mitral valve minimizes the length which the prosthesis and the delivery system protrudes into the left ventricle.

Figure 18:
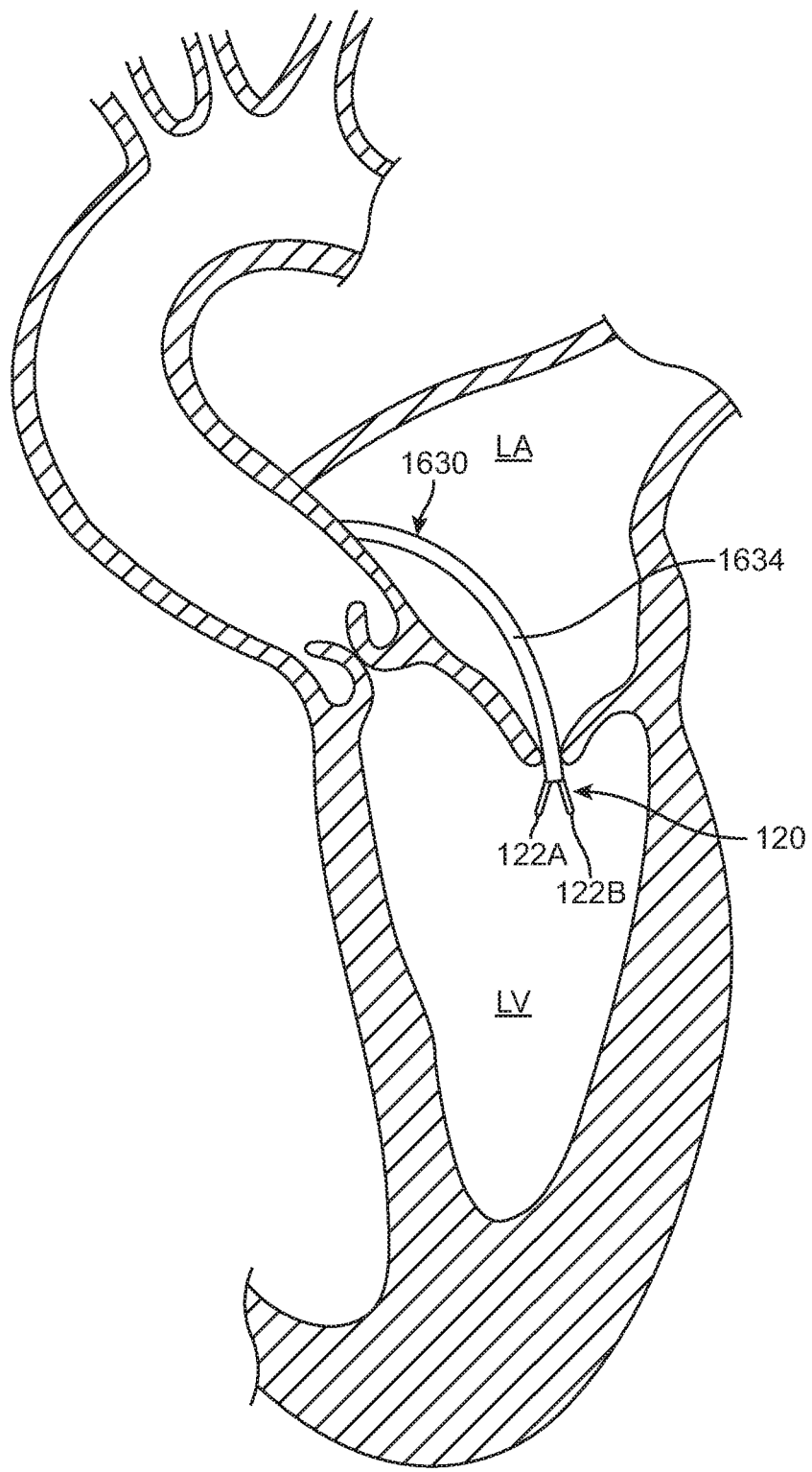

Referring now to FIG. 18, when valve prosthesis 100 is in position in the middle of the native mitral valve, positioning elements 120 of valve prosthesis 100 are released by retracting sheath 1634 of prosthetic valve delivery system 1630 by a sufficient amount that this portion of the prosthesis is exposed. Due to the self-expanding properties of the positioning elements, support arms 122A, 122B will expand radially outwardly relative to the sheath in which it was enclosed. As shown FIG. 18, and also referring to FIG. 8 described above, upon initial release from sheath 1634, positioning elements 120 flare or spread outwardly from the outer surface of the remainder of the prosthesis such that positioning elements 120 are acutely angled with respect to longitudinal axis $L_a$. During the transformation between the distally-extending compressed configuration and the proximally-extending deployed configuration, support arms 122A, 122B are located on outflow side, i.e., the left ventricle LV side, of the mitral valve while stent 102 of prosthesis 100 is positioned within the mitral valve and still contained within sheath 1634.

Figure 19:
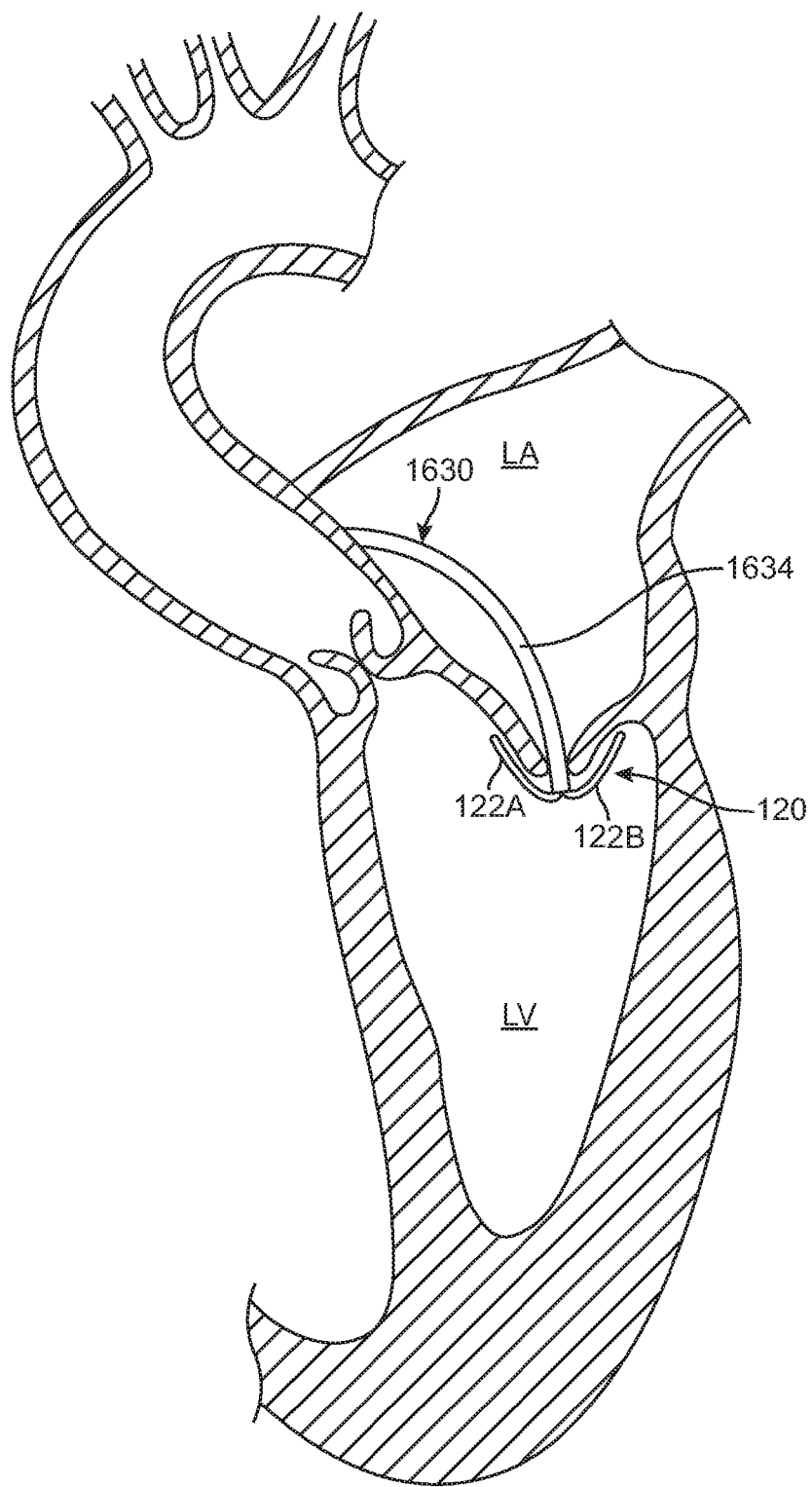

Exposure and rotation of positioning elements 120 continues as sheath 1634 is retracted. FIG. 19 illustrates positioning elements 120 fully exposed or released from sheath 1634 while stent 102 is still compressed within sheath 1634. Positioning elements 120 are now proximally extending, and support arms 122A, 122B firmly press against the native mitral valve leaflets and/or the left ventricle LV in order to position valve prosthesis 100.

Figure 20:
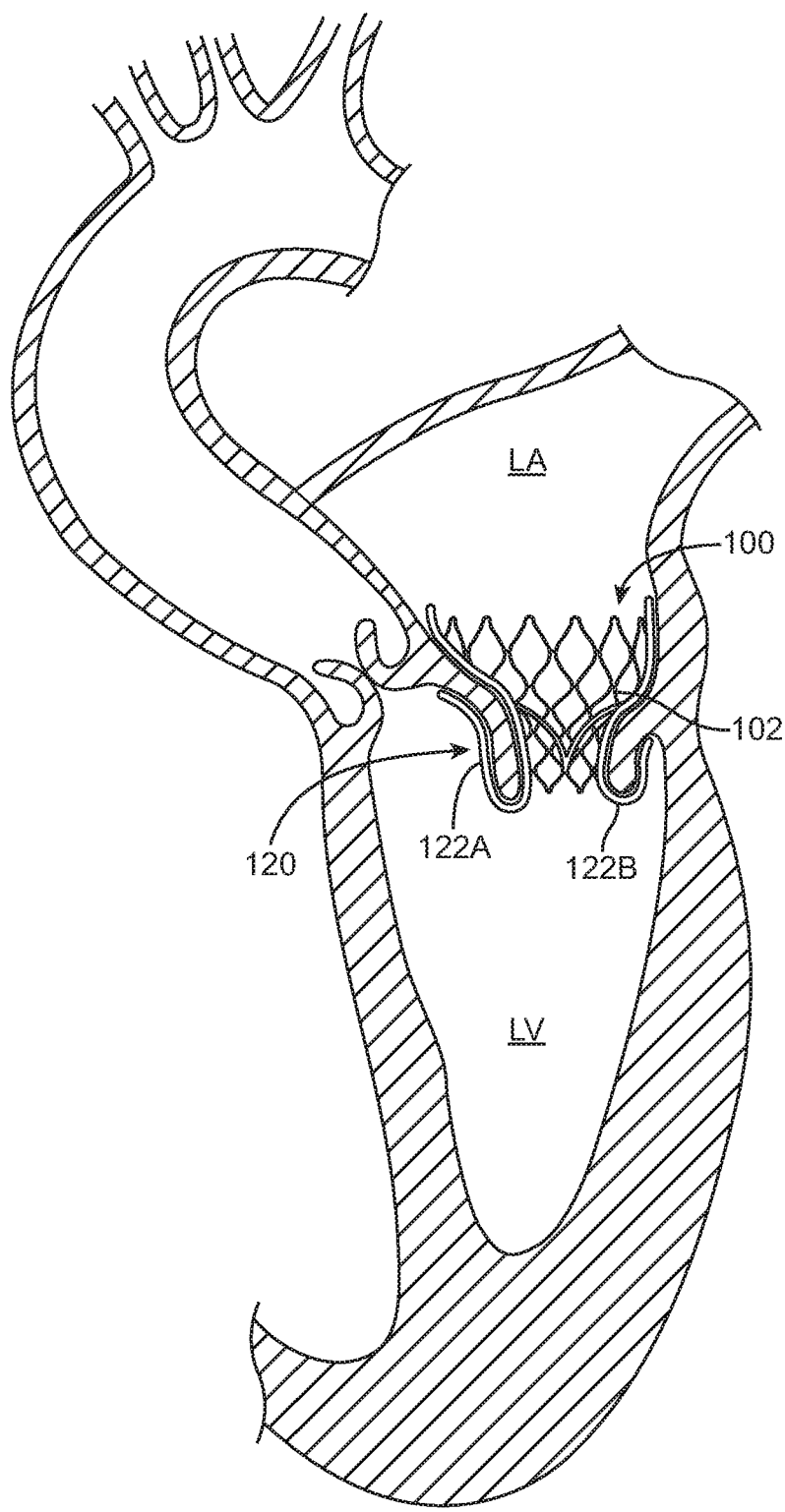

After positioning elements 120 are deployed to anchor or hold valve prosthesis 100 in place as desired, sheath 1634 continues to be proximally retracted, exposing self-expanding stent 102 such that stent 102 is released from the delivery system to assume its deployed configuration. Due to the self-expanding properties of the stent frame, stent 102 will expand outwardly relative to the sheath in which it was enclosed. Sheath 1634 is proximally retracted until the proximal end of stent 102 is exposed and allowed to self-expand, thereby uncoupling the prosthesis from catheter 1632. The delivery system can then be retracted from the patient, leaving the expanded prosthesis 100 deployed at the mitral valve as shown in FIG. 20. In the final deployed configuration of valve prosthesis 100, each positioning element 120 proximally extends from a distal end 104 of stent 102. Each positioning element 120 rotates in a radial direction between 90 and 180 degrees from the initial distally-extending compressed configuration to the final proximally-extending deployed configuration until support arms 122A, 122B firmly press against the native mitral valve leaflets and/or the left ventricle LV in order to position valve prosthesis 100. The amount or degree of rotation may depend upon a patient's individual anatomy and state of the native mitral valve leaflets.

FIGS. 21A, 21B, 22A, 22B illustrates another embodiment of positioning elements with double or dual support arms that may be utilized in any embodiment described herein. More particularly, a valve prosthesis 2100 is shown in its compressed or delivery configuration in the side views of FIG. 21A and FIG. 21B and in its expanded or deployed configuration in the side views of FIG. 22A and FIG. 22B. Similar to embodiments described above, valve prosthesis 2100 includes a framework or stent 2102, a valve component 2116 attached within the interior portion of stent 2102 that is capable of blocking flow in one direction to regulate flow through valve prosthesis 2100 via leaflets 2118A, 2118B, and two positioning elements 2120. Stent 2102 of valve prosthesis 2100 is a generally tubular expandable body having a stepped outer diameter or profile extending between a proximal end 2106 and distal end 2104. Similar to embodiments described above, the stepped outer diameter of stent 2102 includes a distal or ventricular segment 2108 and a proximal or atrial segment 2110 having an expanded diameter which is greater than the expanded diameter of distal segment 2108.

Positioning elements 2120 extend from opposing sides of stent 2102. Each positioning element 2120 includes a first or outer U-shaped support arm 2140A, 2140B, respectfully, and a second or inner U-shaped support arm 2142A that each distally extend from a distal end 2104 of stent 2102. The second or inner U-shaped support arm adjacent to outer U-shaped support arm 2140B is obscured from view in the figures, but it will be understood by those of ordinary skill in the art that each positioning element 2120 includes both an outer U-shaped support arm and an inner U-shaped support arm. When released from a delivery sheath (not shown), each of the U-shaped support arms gradually bends outwardly and then towards an outer surface of the delivery device or stent until they transform from their compressed configuration of FIG. 21A and FIG. 21B to their deployed configuration of FIG. 22A and FIG. 22B in which each of the U-shaped support arms proximally extends from distal end 2104 of stent 2102. As in embodiments described above, each of the U-shaped support arms bends or rotates more than ninety degrees with respect to its compressed, delivery configuration during deployment of valve prosthesis 2100. In one embodiment, each U-shaped support arm rotates between 135 degrees and 180 degrees during deployment of valve prosthesis 2100. Compared to a single U-shaped support arm, outer and inner U-shaped support arms provide each positioning element 2120 with additional spring force for improved anchoring and positioning of the valve prosthesis.

Adjacent outer and inner U-shaped support arms of each positioning element are coupled together via a connector 2144A which ensures that both U-shaped support arms of the positioning element remain in the same plane during deployment. Connector 2144A has a flared V-shaped configuration in which an apex 2145 of connector 2144A is coupled to a peak or crest 2143 of inner support arm 2142A. More particularly, connector 2144A includes two curved legs 2146A, 2146B. First ends of legs 2146A, 2146B are coupled to peak 2143 of inner support arm 2142A, and curved legs 2146A, 2146B of connector 2144A extend or flare away from each other such that second ends of legs 2146A, 2146B are coupled adjacent to or on opposing sides of a peak or crest 2141 of outer support arm 2140A. Due to the curved legs 2146A, 2146B of connector 2144A, the distance or space between the crowns of outer and inner U-shaped support arms is adjustable and allowed to change. Legs 2146A, 2146B allow the distance or space between peak 2143 of inner support arm 2142A and peak 2141 of outer support arm 2140A because the curved legs of connector 2144A may bend, resulting in a shorter distance between peak 2143 and peak 2141, or the legs of connector 2144A may straighten, resulting in a greater distance between peak 2143 and peak 2141. The distance or space between peak 2143 and peak 2141 may increase during crimping when valve prosthesis 2100 is in its compressed configuration shown in FIG. 21A, 21B, and the distance or space may decrease during expansion when valve prosthesis 2100 is in its deployed configuration. Connector 2144A, as well as the inner and outer U-shaped support arms, may be laser cut from a tube of self-expanding material and thereby integrally formed as part of the stent, or may be formed separately and subsequently attached to the stent. Although connector 2144A is only visible in FIGS. 21A, 21B, 22A, 22B between inner support arm 2142A and outer support arm 2140A, it will be understood by those of ordinary skill in the art that such a connector couples the outer and inner support arms of each positioning element extending from the prosthesis.

FIGS. 23A, 23B, 23C illustrate an embodiment of a valve prosthesis 2300 including a lattice framework or stent 2302 and positioning elements 2320 with dual U-shaped support arms that distally extend from a distal end 2304 of the valve prosthesis. More particularly, positioning elements 2320 include a first or outer U-shaped support arm 2340A, 2340B, respectfully, and a second or inner U-shaped support arm 2342A, 2342B that each bend or rotate more than ninety degrees with respect to its compressed, delivery configuration during deployment. Each outer support arm is connected to its respective inner support arm via a connector 2344A, as described above with respect to connector 2144A. In the embodiment of FIGS. 23A, 23B, 23C, the U-shaped support arms extend from the distalmost crowns or apexes 2353 of lattice stent 2302. Compared to the embodiment shown in FIGS. 24A-24C, stent 2302 has a smaller crimped profile for delivery.

FIGS. 24A, 24B, 24C illustrate an embodiment of a valve prosthesis 2400 that is similar to valve prosthesis 2300, except that positioning elements 2420 do not extend from distalmost crowns or apexes 2453 of a lattice stent 2402. Rather, the positioning elements extend from between the distalmost crowns or apexes 2453 of lattice stent 2402. As best shown in FIG. 24B, in order to shorten or minimize the open space or distance 2450 between adjacent positioning elements 2420, positioning elements 2420 extend from opposing sides of a distalmost crown 2453 such that the positioning elements are separated only by the width of the crown. More particularly, positioning elements 2420 distally extend from a distal end 2404 of the valve prosthesis and include a first or outer U-shaped support arm 2440A, 2440B, respectfully, and a second or inner U-shaped support arm 2442A, 2442B that each bend or rotate more than ninety degrees with respect to its compressed, delivery configuration during deployment. Each outer support arm is connected to its respective inner support arm via a connector 2444A, as described above with respect to connector 2144A. Positioning elements 2420 extend from between the distalmost crowns or apexes 2453 of lattice stent 2402 to minimize open space or distance 2450 and thereby prevent the prosthetic valve leaflets from obstructing the outflow end of valve prosthesis 2400 and the left ventricular outflow tract (LVOT). Outer U-shaped support arms of the positioning elements are closer together, and act as an obstacle in the path that the prosthetic valve leaflets would follow when overlapping onto stent 2402 and thereby keeps the flow path clear. Another benefit of extending positioning elements 2420 from between the distalmost crowns or apexes 2453 of lattice stent 2402 is that the positioning elements are located more proximal along the prosthesis compared to the embodiment shown in FIGS. 23A-23C, which minimizes the length or amount of material that projects or extends in the left ventricle.

Figure 25B:
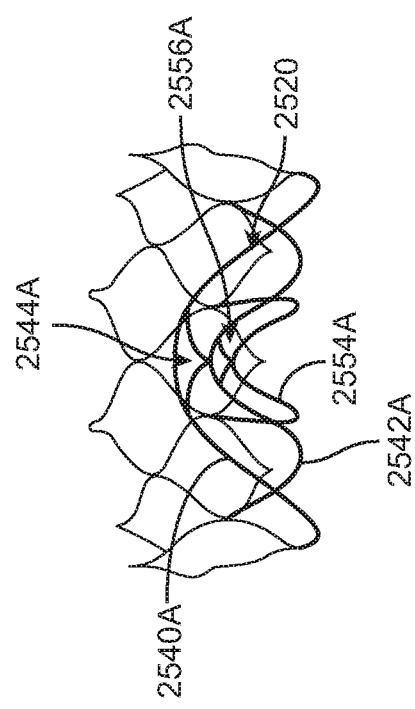
FIG. 25B is an enlarged view of a portion of the valve prosthesis of FIG. 25A.
Figure 25A:
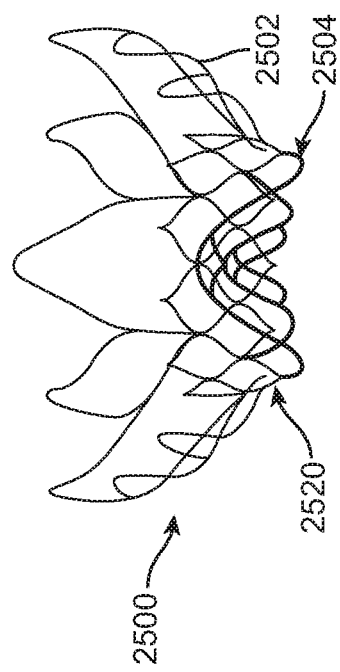
FIG. 25A is a side view of a valve prosthesis having positioning elements with triple U-shaped support arms according to an embodiment hereof, wherein the valve prosthesis is in an expanded or deployed configuration.

FIGS. 25A and 25B illustrate another embodiment of a valve prosthesis 2500 that is similar to valve prosthesis 2400, except that each positioning element 2520 includes triple support arms for additional spring force for improved anchoring and positioning of the valve prosthesis. Each positioning element 2520 extends from between the distalmost crowns of a distal end 2504 of a lattice stent 2502 and includes a first or outer U-shaped support arm 2540A, a second or intermediate U-shaped support arm 2542A, and a third or inner U-shaped support arm 2554A. When released from a delivery sheath (not shown in FIG. 25A or FIG. 25B), all of the U-shaped support arms gradually bend outwardly and then towards an outer surface of the delivery device or stent until they reach their deployed configuration of FIG. 25A and FIG. 25B in which all of the U-shaped support arms proximally extend from distal end 2504 of stent 2502. As in embodiments described above, all of the U-shaped support arms bend or rotate more than ninety degrees with respect to its compressed, delivery configuration during deployment of valve prosthesis 2500. In one embodiment, each U-shaped support arm rotates between 135 degrees and 180 degrees during deployment of valve prosthesis 2100. Although only one positioning element is shown in described in FIGS. 25A, 25B, it will be understood by those of ordinary skill in the art that valve prosthesis 2500 includes at least two positioning elements extending from opposing sides of the prosthesis. Each positioning element includes triple U-shaped support arms for anchoring and positioning the valve prosthesis.

Adjacent U-shaped support arms of each positioning element are coupled together via a connector which ensures that each support arm of the positioning element remains in the same plane during deployment. More specifically, outer U-shaped support arm 2540A is coupled to intermediate U-shaped support arm 2542A via a connector 2544A and intermediate U-shaped support arm 2542A is coupled to inner U-shaped support arm 2554A via a connector 2556A. Connectors 2544A, 2556A have the same flared V-shaped configuration as connector 2144A described above. Due to the curved or flared legs of connectors 2544A, 2556A, the distance or space between the peaks of adjacent U-shaped support arms is adjustable and allowed to change as described with respect to connector 2144A.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, although support arms of various embodiments are described herein as U-shaped, it will be understood by one of ordinary skill in the art that any support arm described herein may be generally U-shaped or V-shaped as shown in FIGS. 26A-26F. In addition, valve prostheses described here may include more than two positioning elements that transform from an initial distally-extending compressed configuration to a final proximally-extending deployed configuration. A minimum of two positioning elements are required such that a support arm is positioned behind each leaflet of a native mitral valve. However, additional positioning elements may be included without departing from the spirit and scope of the invention. In one embodiment, four positioning elements may be circumferentially disposed around the perimeter of a stent that supports a prosthetic bileaflet valve therein. In another embodiment, three positioning elements may be circumferentially disposed around the perimeter of a stent that supports a prosthetic trileaflet valve therein.

In addition to variations of the positioning elements, various changes in form and detail can be made to the stent of the valve prosthesis without departing from the spirit and scope of the invention. As previously described, the stent frame may have any suitable configuration known in the art. In addition, although not required, portions of the stent may be selectively plated with platinum or other biocompatible material to provide improved visibility during fluoroscopy and thereby aid in positioning the stent in the middle of the mitral valve for deployment. In one embodiment of the present invention, one or more radiopaque markers (not shown) may be attached to the valve prosthesis at one or more predetermined locations. The marker may be formed of platinum or any other relatively heavy metal, which may be generally visible by X-ray fluoroscopy.

Accordingly, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of percutaneously delivering and deploying a valve prosthesis within a native heart valve comprising:
    tracking a prosthetic valve delivery system through the vasculature to the native heart valve, wherein the prosthetic valve delivery system includes a valve prosthesis having a tubular stent, a prosthetic valve component disposed within and secured to the tubular stent, and at least one positioning element coupled to a distal end of the tubular stent, the at least one positioning element having an outer support arm having first and second ends and an inner support arm having first and second ends, the outer and inner support arms extending distally from the distal end of the tubular stent when the tubular stent is in a compressed configuration for delivery, the outer and inner support arms extending along the same plane and the inner support arm being disposed within the outer support arm such that portions of the inner and outer support arms are aligned and the first and second ends of the outer support arm being coupled to the tubular stent at a circumferentially spaced apart location from the respective first and second ends of the inner support arm;
    retracting an outer sheath of the prosthetic valve delivery system to expose the at least one positioning element, wherein each of the outer support arm and the inner support arm bends radially outward and then towards an outer surface of the tubular stent such that it translates more than ninety degrees from the compressed configuration to proximally extend from the distal end of the tubular stent and press against the native heart valve and/or a heart wall in order to position the valve prosthesis within the native heart valve; and
    further retracting the outer sheath to expose the tubular stent, thereby allowing the tubular stent to self-expand into a deployed configuration.

2. The method of claim 1, wherein the native heart valve is percutaneously accessed by a transseptal antegrade approach.

3. The method of claim 1, wherein the step of tracking the prosthetic valve delivery system through the vasculature to the native heart valve includes advancing the prosthetic valve delivery system into an atrium until the valve prosthesis is centered within the native heart valve with the at least one positioning element contained within the outer sheath and distally extending into a ventricle.

4. The method of claim 1, wherein the tubular stent is contained within the outer sheath during the step of retracting the outer sheath to expose the at least one positioning element.

5. The method of claim 1, wherein the at least one positioning element rotates in a radial direction between 135 degrees and 180 degrees from the compressed configuration during deployment of the valve prosthesis.

6. The method of claim 1, wherein the outer support arm is connected to the inner support arm by two curved legs, wherein first ends of the two curved legs extend from a peak of the inner support arm and the two curved legs flare away from each other such that second ends of the two curved legs extend from opposing sides of a peak of the outer support arm.

7. The method of claim 6, wherein the distance between the peaks of the inner support arm and the outer support arm decreases when the at least one positioning element rotates from the compressed configuration to the deployed configuration.

8. The method of claim 1, wherein the at least one positioning element includes an intermediate U-shaped or V-shaped support arm between the outer support arm and the inner support arm.

9. The method of claim 1, wherein the inner and outer support arms are generally U-shaped or V-shaped.

10. The method of claim 1, wherein the inner and outer support arms each have a peak formed between their first and second ends, wherein the peak of the outer support arm is coupled to the peak of the inner support arm via a connector to ensure that the outer and inner support arms remain in the same plane.

11. A method of percutaneously delivering and deploying a valve prosthesis within a native heart valve comprising:
    tracking a prosthetic valve delivery system through the vasculature to the native heart valve, wherein the prosthetic valve delivery system includes a valve prosthesis having a tubular stent, a prosthetic valve component disposed within and secured to the tubular stent, and at least one positioning element coupled to a distal end of the tubular stent, the at least one positioning element distally extending from the distal end of the tubular stent when the tubular stent is in a compressed configuration and the at least one positioning element including an outer support arm having a first end and a second end coupled to the distal end of the tubular stent with a peak formed between the first and second ends and an inner support arm having a first end and a second end coupled to the distal end of the tubular stent with a peak formed between the first and second ends, the outer and inner support arms extending along the same plane and the inner support arm being disposed within the outer support arm such that the peaks of the inner and outer support arms are aligned and each of the first and second ends of the outer support arm is coupled to the tubular stent at a circumferentially spaced apart location from the respective first and second ends of the inner support arm;

retracting an outer sheath of the prosthetic valve delivery system to expose the at least one positioning element, wherein each of the outer and inner support arm bends radially outward and then towards an outer surface of the tubular stent such that it translates more than ninety degrees from the compressed configuration to proximally extend from the distal end of the tubular stent and press against a portion of the native heart valve and/or a portion of a native heart wall in order to position the valve prosthesis, wherein the peak of the outer support arm is coupled to the peak of the inner support arm via a connector to ensure that the outer and inner support arms remain in the same plane; and further retracting the outer sheath to expose the tubular stent, thereby allowing the tubular stent to self-expand into a deployed configuration.

12. The method of claim 11, wherein the native heart valve is percutaneously accessed by a transseptal antegrade approach.

13. The method of claim 11, wherein the step of tracking the prosthetic valve delivery system through the vasculature to the native heart valve includes advancing the prosthetic valve delivery system into an atrium until the valve prosthesis is centered within the native valve with the at least one positioning element contained within the outer sheath and distally extending into a ventricle.

14. The method of claim 11, wherein the tubular stent is contained within the outer sheath during the step of retracting the outer sheath to expose the at least one positioning element.

15. The method of claim 11, wherein the at least one positioning element rotates in a radial direction between 135 degrees and 180 degrees from the compressed configuration during deployment of the valve prosthesis.

16. The method of claim 11, wherein the connector that couples the peaks of the outer and inner support arms together includes two curved legs, wherein first ends of the two curved legs extend from the peak of the inner support arm and the two curved legs flare away from each other such that second ends of the two curved legs extend from opposing sides of the peak of the outer support arm.

17. The method of claim 16, wherein the distance between the peaks of the inner support arm and the outer support arm decreases when the at least one positioning element rotates from the compressed configuration to the deployed configuration.

18. The method of claim 11, wherein the at least one positioning element includes an intermediate support arm between the outer support arm and the inner support arm, the intermediate support arm having a first end and a second end coupled to the distal end of the tubular stent with a peak formed between the first and second ends.

19. The method of claim 18, wherein the intermediate support arm extends along the same plane as the outer and inner support arms and is disposed between the outer support arm and the inner support arm such that the peaks of the inner, outer, and intermediate support arms are aligned.

20. The method of claim 11, wherein the outer and inner support arms are generally U-shaped or V-shaped.

21. The method of claim 11, wherein the at least one positioning element is approximately parallel with a longitudinal axis of the tubular stent and distally extends from the distal end of the tubular stent when the tubular stent is in the compressed configuration.

22. The method of claim 11, wherein the tubular stent and the at least one positioning element are formed as a unitary structure.

* * * * *